(12) United States Patent
Gronthos et al.

(10) Patent No.: US 9,169,466 B2
(45) Date of Patent: Oct. 27, 2015

(54) PERIVASCULAR MESENCHYMAL PRECURSOR CELL INDUCED BLOOD VESSEL FORMATION

(75) Inventors: Stan Gronthos, Colonel Light Gardens (AU); Andrew Zannettino, Highbury (AU)

(73) Assignee: MESOBLAST, INC., New York, NY (US)

( * ) Notice: Subject to any disclaimer, the term of this patent is extended or adjusted under 35 U.S.C. 154(b) by 652 days.

(21) Appl. No.: 10/551,326

(22) PCT Filed: Mar. 29, 2004

(86) PCT No.: PCT/AU2004/000417
§ 371 (c)(1),
(2), (4) Date: Mar. 20, 2006

(87) PCT Pub. No.: WO2004/084921
PCT Pub. Date: Oct. 7, 2004

(65) Prior Publication Data
US 2006/0286077 A1    Dec. 21, 2006

(30) Foreign Application Priority Data
Mar. 28, 2003 (AU) .................................. 2003901668

(51) Int. Cl.
| | |
|---|---|
| A01N 63/00 | (2006.01) |
| C12N 5/00 | (2006.01) |
| C12N 5/071 | (2010.01) |
| A61K 35/28 | (2015.01) |
| C12N 5/0775 | (2010.01) |
| A61K 35/44 | (2015.01) |
| A61K 38/00 | (2006.01) |

(52) U.S. Cl.
CPC .............. *C12N 5/0691* (2013.01); *A61K 35/28* (2013.01); *A61K 35/44* (2013.01); *C12N 5/0668* (2013.01); *A61K 38/00* (2013.01); *C12N 2500/42* (2013.01); *C12N 2501/39* (2013.01); *C12N 2506/1392* (2013.01)

(58) Field of Classification Search
CPC ....... A61K 35/28; A61K 35/44; C12N 5/0691
See application file for complete search history.

(56) References Cited

U.S. PATENT DOCUMENTS

| | | |
|---|---|---|
| 5,197,985 A | 3/1993 | Caplan et al. |
| 5,226,914 A | 7/1993 | Caplan et al. |
| 5,405,772 A | 4/1995 | Ponting et al. |
| 5,486,359 A | 1/1996 | Caplan et al. |
| 5,580,754 A | 12/1996 | Samal |
| 5,591,625 A | 1/1997 | Gerson et al. |
| 5,811,094 A | 9/1998 | Caplan et al. |
| 5,827,740 A | 10/1998 | Pittenger |
| 5,837,539 A | 11/1998 | Caplan et al. |
| 5,922,597 A | 7/1999 | Verfaille et al. |
| 5,980,887 A | 11/1999 | Isner et al. |
| 6,022,540 A | 2/2000 | Bruder et al. |
| 6,087,113 A | 7/2000 | Caplan et al. |
| 6,261,549 B1 | 7/2001 | Fernandez et al. |
| 6,322,784 B1 | 11/2001 | Pittenger et al. |
| 6,335,195 B1 | 1/2002 | Rodgers et al. |
| 6,387,367 B1 | 5/2002 | Davis-Sproul et al. |
| 6,387,369 B1 | 5/2002 | Pittenger et al. |
| 6,645,727 B2 | 11/2003 | Thomas et al. |
| 6,709,864 B1 | 3/2004 | Pittinger et al. |
| 6,875,430 B2 | 4/2005 | McIntosh et al. |
| 7,122,178 B1 | 10/2006 | Simmons et al. |
| 7,470,538 B2 | 12/2008 | Laughlin et al. |
| 7,947,266 B2 | 5/2011 | Gronthos et al. |
| 8,062,675 B2 | 11/2011 | Gronthos et al. |
| 8,158,118 B2 | 4/2012 | Simmons et al. |
| 2002/0085996 A1 | 7/2002 | McIntosh et al. |
| 2004/0107453 A1 | 6/2004 | Furcht et al. |
| 2005/0019911 A1 | 1/2005 | Gronthos et al. |
| 2005/0158289 A1 | 7/2005 | Simmons et al. |
| 2005/0271639 A1 | 12/2005 | Penn et al. |
| 2005/0281790 A1 | 12/2005 | Simmons et al. |
| 2006/0008452 A1 | 1/2006 | Simmons et al. |

(Continued)

FOREIGN PATENT DOCUMENTS

| | | | |
|---|---|---|---|
| AU | WO 01/04268 | * | 1/2001 |
| WO | WO 99/03973 A | | 1/1999 |

(Continued)

OTHER PUBLICATIONS

Barry et al ., 2003, Birth Defect Research (Part C) 69:250-256 Pittenger et al., (1999, WO 99/03973).*
Kassem et al., 2004, Cloning Stem Cells 6:369-374.*
Le Blanc et al., 2005, Biology of Blood and marrow transplantation 11:321-334.*
Summer et al., 2008, Proc. Am, Thorac. Soc 5:707-710.*
Jones et al., 2002, Arthritis and Rheumatism 46:3349-3360.*
Chopp et al., 2002, The Lancet Neurology 1:92-100.*
Bianco et al 2001, Stem cells 19:180-192.*
Dennis et al., 2002, Cells Tissues Organs 170:73-82 (Abstract p. 1-2).*
Reyes et al., 2002, Clin. Invest. 109:337-346.*
Kocher et al., 2001, Nature Medicine 7:430-436.*

(Continued)

*Primary Examiner* — Christopher M Babic
*Assistant Examiner* — Kelaginamane T Hiriyanna
(74) *Attorney, Agent, or Firm* — John P. White; Cooper & Dunham LLP

(57) ABSTRACT

Mesenchymal precursors cells have been isolated from perivascular niches from a range of tissues utilizing a perivascular marker. A new mesenchymal precursor cell phenotype is described characterized by the presence of the perivascular marker 3G5, and preferably also alpha smooth muscle actin together with early developmental markers such as STRO-1 and CD146/MUC18. The perivascular mesenchymal precursor cell is shown to induce neovascularization and improvement in cardiac function. Suitable administration of preparations of the mesenchymal precursor cells are useful for treatment of cardiovascular diseases, cerebrovascular diseases and peripheral vascular diseases.

36 Claims, 26 Drawing Sheets

(56) References Cited

U.S. PATENT DOCUMENTS

| | | |
|---|---|---|
| 2006/0193840 A1 | 8/2006 | Gronthos et al. |
| 2007/0065938 A1 | 3/2007 | Gronthos et al. |
| 2007/0274958 A1 | 11/2007 | Shi et al. |

FOREIGN PATENT DOCUMENTS

| | | |
|---|---|---|
| WO | WO 00/06701 | 2/2000 |
| WO | WO 01/07679 A2 | 1/2001 |
| WO | WO 01/11011 | 2/2001 |
| WO | WO 02/07679 | 1/2002 |
| WO | WO 02/07679 A2 | 1/2002 |
| WO | WO 03/016916 | 2/2003 |
| WO | WO 2004/084921 A1 | 10/2004 |
| WO | WO 2004/085630 A1 | 10/2004 |

OTHER PUBLICATIONS

U.S. Appl. No. 11/663,570, filed Mar. 23, 2007.
U.S. Appl. No. 11/663,563, filed Mar. 23, 2007.
Alberico et al. (1987) Blood 69, p. 1120.
Allen, T.D., (1981) "Haemopoietic Microenvironments in vitro:ultrastructural aspects" CIBA Found. Symposium 84, pp. 38-67.
Allen et al. (1990) "Marrow Biology and Stem Cells" Immunol. Ser. 49, pp. 1-38.
Anklesaria et al. (1989) Blood 74, p. 1144.
Anklesaria et al. (1987) Proc. Nat'l Acad. Sci. USA 84, p. 7681.
Bennett, J.H. et al. (1991) J. Cell Sci. 99, p. 131.
Bentley, S.A. (1982) Br. J. Haematol 50(1), pp. 1-6.
Castro-Malaspina et al. (1980) "Characterization of Human Bone Marrow Fibroblast Colony-Forming Cells and Their Progeny" Blood 56, pp. 289-301.
Castro-Malaspina et al. (1981) "Human Megakaryocyte Stimulation of Proliferation of Bone Marrow Fibroblasts" Blood 57, pp. 781-787.
Clarke, Emer, "Mesenchymal Cells" www.stemcell.com (mini-review).
Dexter et al. (1977) "Conditions Controlling the Proliferation of Haemopoietic Stem Cells in Vitro" J. Cell Physiol. 91, pp. 335-344.
Dexter et al. (1984) Kroc Found. Ser. 18, pp. 57-96.
Doherty, M.J. et al. (1998) "Vascular Pericytes Express Osteogenic Potential In Vitro and In Vitro" J. Bone and Mineral Research 13, pp. 828-838.
Fong et al. (1997) "Nonradioactive, Agarose Minigel Procedure for Telomeric Repeat Amplification Protocol" BioTechniques 23, pp. 1029-1032.
Friedenstein (1976) Int'l R. Cytology 47, p. 327.
Friedenstein (1980) "Stromal Mechanisms of Bone Marrow: Cloning in Vitro and Retransplantation in Vivo" Immunology of Bone Marrow Transplantation, pp. 19-29 Haematol. Blood Transfusion.
Friedenstein et al. (1970) "The Development of Fibroblast Colonies in Monolayer Cultures of Guinea-Pig Bone Marrow and Spleen Cells" Cell Tissue Kinetics 3, pp. 393-403.
Friedenstein et al. (1992) Bone and Mineral 18, pp. 199-213.
Gronthos, S. et al. (2002) "Stem Cell Properties of Human Dental Pulp Stem Cells" J. Dent. Res. 81(8), pp. 531-535.
Gronthos, S., et al. (1994) "The STRO-1+ Fraction of Adult Human Bone Marrow Contains the Osteogenic Precursors," Blood 84, pp. 4164-4173.
Gronthos, S., et al. (1995) Blood 85, pp. 929-940.
Huang and Terstappen (1992) Nature 360, pp. 745-749.
Keating et al. (1982) Nature 298, pp. 280-283.
Kim et al. (1994) Science 266, pp. 2011-2015.
Knospe et al. (1966) Blood 28, pp. 398-415.
Knospe et al. (1972) Blood 39, pp. 331-340.
Lichtman (1981) Experimental Hematology 9, pp. 391-410.
Long (1992) Experimental Hematology 20, pp. 288-301.
McManus and Weiss (1984) Blood 64, pp. 1036-1041.
McIntyre and Bjornson (1986) Exp. Hematol. 14, pp. 833-839.
Miltenyi et al. (1990) Cytometry 11, pp. 231-238.
Owen (1985) Bone and Mineral Research 3, pp. 1-25.
Owen and Friedenstein (1988) CIBA Found. Symposium 136, pp. 42-60.
Perkins and Fleischman (1990) Blood 75, pp. 620-625.
Piersma et al. (1983) Br. J. Haematol. 54, pp. 285-290.
Rothstein et al. (1985) Blood 65, p. 744.
Simmons and Gronthos (1991) Int'l J. Cell Cloning 9, p. 408 (abstract).
Simmons, P.J., et al. (1994) "Isolation, Characterization and Functional Activity of Human Marrow Stromal Progenitors in Hemopoiesis" Advances in Bone Marrow Purging and Processing: Progress in Clinical and Biological Research; Fourth Int'l Symposium 389, pp. 271-280.
Simmons et al. (1987) Nature 328, pp. 429-432.
Simmons and Torok-Storb (1991) Blood 78, pp. 55-62.
Simmons and Torok-Storb (1991) Blood 78, pp. 2848-2853.
Tavassoli and Friedenstein (1983) Ann. J. Hematol. 15, pp. 195-203.
Tavassoli and Crosby (1968) Science 161, pp. 54-56.
Testa et al. (1988) "Long-Term Bone Marrow Damage After Cytotoxic Treatment: Stem Cells and Microenvironment in Hematopoiesis: Long-Term Effects of Chemotherapy and Radiation" Hematol. Published by Marcel & Deaker, Inc. 8, pp. 75-91.
Van Vlasselaer et al. (1994) Blood 84, p. 753-763.
Waller et al. (1995) Blood 85, p. 2422-2435.
Weiss (1976) Anatomical Record 186, p. 161-184.
Axelrad et al., New Technologies for the Enhancement of Skeletal Repair, Injury, Int. J. Care Injured (2007) 38S1:S49-S62.
Bruder et al., Mesenchymal Stem Cells in Bone Development, Bone Repair, and Skeletal Regeneration Therapy, J. Cell Biochem; (1994) 56:283-294.
Dennis et al., Osteogenesis in Marrow-Derived Mesenchymal Cell Porous Ceramic Composites Transplanted Subcutaneously: Effect of Fibronectin and Laminin on Cell Retention and Rate of Osteogenic Expression, Cell Transplant (1992) 1:23-32, Abstract.
Zvaifler, et al., (2000) "Mesenchymal precursor cells in the blood of normal individuals," Arthritis Research and Therapy, 2: 477-488.
Ji, et al., (2004) "Interactions of Chemokines and Chemokine Receptors Mediate the Migration of Mesenchymal Stem Cells to the Impaired Site in the Brain After Hypoglossal Nerve Injury," Stem Cells, 22: 415-427.
Sordi, et al., (2005) "Bone marrow mesenchymal stem cells express a restricted set of functionally active chemokine receptors capable of promoting migration to pancreatic islets," Blood, 106(2): 419-427.
Wynn, et al., (2004) "A small proportion of mesenchymal stem cells strongly expresses functionally active CXCR4 receptor capable of promoting migration to bone marrow," Blood, 104(9): 2643-2645.
Kortesidis, et al., (2005) "Stromal-derived factor-1 promotes the growth, survival, and development of human bone marrow stromal stem cells," Blood, 105(10): 3793-3801.
Gronthos, S., et al., (1999) "Differential Cell Surface Expression of The STRO-1 and Alkaline Phosphatase Antigens on Discrete Developmental Stages in Primary Culture of Human Bone Cells," Journal of Bone and Mineral Research, 14(1): 47-56.
Stewart, K., et al., (1999) "Further Characterization of Cells Expressing STRO-1 in Cultures of Adult Human Bone Marrow Stromal Cells," Journal of Bone and Mineral Research, 14(8): 1345-1356.
International Search Report issued by the International Searching Authority (ISA/AU) on May 17, 2004 in connection with International Application No. PCT/AU2004/000416.
International Preliminary Report on Patentability issued by the International Bureau of WIPO on Oct. 1, 2005 in connection with International Application No. PCT/AU2004/000416.
International Search Report issued by the International Searching Authority (ISA/AU) on Aug. 22, 2005 in connection with International Application No. PCT/AU2005/000953.
International Search Report issued by the International Searching Authority (ISA/AU) on Nov. 25, 2005 in connection with International Application No. PCT/AU2005/001445.
Office Action issued Jan. 12, 2005 in connection with U.S. Appl. No. 10/030,411.
Office Action issued Jun. 28, 2005 in connection with U.S. Appl. No. 10/030,411.
Final Office Action issued Jan. 9, 2006 in connection with U.S. Appl. No. 10/030,411.

(56) References Cited

OTHER PUBLICATIONS

Office Action issued Apr. 20, 2007 in connection with U.S. Appl. No. 10/955,709.
Office Action issued Aug. 24, 2007 in connection with U.S. Appl. No. 11/178,920.
Office Action issued Aug. 25, 2006 in connection with U.S. Appl. No. 110/955,709.
Examiner Interview Summary issued Jun. 27, 2006 in connection with U.S. Appl. No. 10/030,411.
Office Action issued Dec. 15, 2006 in connection with U.S. Appl. No. 11/178,920.
Office Action issued Jul. 10, 2006 in connection with U.S. Appl. No. 11/178,920.
Office Action issued Jan. 22, 2007 in connection with U.S. Appl. No. 11/169,875.
Office Action issued Jul. 10, 2006 in connection with U.S. Appl. No. 10/813,747.
Office Action issued Dec. 15, 2006 in connection with U.S. Appl. No. 10/813,747.
Office Action issued Apr. 3, 2007 in connection with U.S. Appl. No. 10/813,747.
Office Action issued Oct. 19, 2007 in connection with U.S. Appl. No. 10/813,747.
Restriction Requirement issued Jan. 8, 2008 in connection with U.S. Appl. No. 10/551,162.
Final Office Action issued Jan. 10, 2008 in connection with U.S. Appl. No. 10/955,709.
Restriction Requirement issued Jan. 8, 2008 in connection with U.S. Appl. No. 11/326,736.
Extended European Search Report issued Dec. 27, 2007 in connection with European Application No. 05787106.3.
Supplementary European Search Report issued Jan. 2, 2008 in connection with European Application No. 05754008.0.
Cochlovius, B. et al. (2003) "Therapeutic Antibodies," Modern Drug Discovery pp. 33-34, 37-38.
Gronthos et al. Journal of Hematotherapy, 1996. 5, 15-23 (Abstract).
Hansson, M. et al. (2007) "Commentary: Isolated Stem Cells—Patentable as Cultural Artifacts?" V.25, pp. 1507-1510.
Pan, Beiqing et al. (2004) "The nitrogen-containing bisphosphonate, zaledronic acid, increases mineralisation of human bone-derived cells in vitro." *Bone* 34:112-123.
Cassiede, P. et al. (1996) "Osteochondrogenic Potential of Marrow Mesenchymal Progenitor Cells Exposed to TGF-β1 or PDGF-BB as Assayed In Vivo and In Vitro" *Journal of Bone and Mineral Research* vol. 11(9):1264-1273.
Kang Yong Jung et al. (2004) "Involvement of PI-3-kinase, JNK, PKC, and PKA in the PDGF-induced proliferation in himan adipose tissue-derived mesenchymal stem cells" vol. 18(8) p. C253.
International Search Report issued by the International Searching Authority (ISA/AU) on May 17, 2004 in connection with International Application No. PCT/AU2004/000417.
Hellstrom M, Kalen M, Lindahl P, Abramsson A, and Betsholtz C. (1999) Role of PDGF-B and PDGFR-beta in recruitment of vascular smooth muscle cells and pericytes during embryonic blood vessel formation in the mouse. Development 126: 3047-3055.
Zoltowska A, Stepinski J, Lewko B, Zamorska B, Roszkiewicz A, Serkies K, and Kruszewski WJ. (2001) Malformations of Angiogenesis in the Low Differentiated Human Carcinomas. Immunohistorical Study. Arch. Immunol. Ther. Ex. 49: 59-61.
Shi S and Gronthos S. (2003) Perivascular Niche of Postatal Mesenchymal Stem Cells in Human Bone Marrow and Dental Pulp. J. Bone Miner. Res. 18(4): 696-704.
International Preliminary Report on Patentability issued by the International Bureau of WIPO on Oct. 1, 2005 in connection with International Application No. PCT/AU2004/00417.
Shi S et al: "Perivascular niche of postnatal mesenchymal stem cells in human bone marrow and dental pulp." Journal of Bone and Mineral Research, vol. 17, No. Suppl 1, Sep. 2002, p. S446, XP009083412 & Twenty-Fourth Annual meeting of the American Society for Bone and Mineral Research; San Antonio, Texas, USA; Sep. 20-24, 2002.
Tse H F et al: "Angiogenesis in ischaemic myocardium by intramyocardial autologous bone marrow mononuclear cell implantation." Lancet The, Lancet Limited, London, GB, vol. 361, No. 9351, Jan. 4, 2003, pp. 47-49.
Jones Elena A et al: "Isolation and characterization of bone marrow multipotential mesenchymal progenitor cells." Arthritis and Rheumatism Dec. 2002, vol. 46, No. 12, Dec. 2002, pp. 3349-3360.
Gronthos S et al: "Postnatal human dental pulp stem cells (DPSCs) in vitro and in vivo." Proceedings of the National Academy of Sciences of USA, National Academy of Science, Washington, DC, US, vol. 97, No. 25, Dec. 5, 2000, pp. 13625-13630.
Shi S et al: "Comparison of human dental pulp and bone marrow stromal stem cells by cDNA microarray analysis." Bone, Pergamon Press., Oxford, GB, vol. 29, No. 6, Dec. 2001, pp. 532-539.
Gronthos S et al: "Molecular and cellular characterization of highly purified stromal stem cells derived from human bone marrow." Journal of Cell Science, vol. 116, No. 9, May 1, 2003, pp. 1827-1835.
Shi S et al: "Perivascular niche of postnatal mesenchymal stem cells in human bone marrow and dental pulp." Journal of Bone and Mineral Research, New York, NY, US, vol. 18, No. 4, Apr. 2003, p. 696-704.
Supplementary European Search Report from European Patent Office, Application No. EP 04 72 3937, May 25, 2007.
Supplementary European Search Report from European Patent Office, Application No. EP 04 72 3935, May 10, 2007.
Restriction Requirement issued Nov. 13, 2007 in connection with U.S. Appl. No. 11/169,875.
Finney, M.R. et al. (2006) Direct Comparison of Umbilical Cord Blood versus Bone Marrow-Derived Endothelial Precursor Cells in . . . Biol. Blood and Marrow Transplant 12:585-59.
Greenberger, J. and Keating, A. (1996) "The Hematopoietic Effects Microenvironment." Keystone Symposium, Taos, New Mexico 14:366-367.
Murray et al. (1996) "Fetal Bone Marrow CD34+CD41+ Cells are Enriched for Multipotent Hematopoietic Progenitors, but not for Pluripotent Stem Cells." Exp. Hematol. 24:236-245.
Nov. 13, 2007 Restriction Requirement issued in connection with U.S. Appl. No. 11/169,875.
Sep. 12, 2008 Office Action issued in connection with U.S. Appl. No. 10/551,162.
Oct. 16, 2008 Office Action issued in connection with U.S. Appl. No. 10/955,709.
Nov. 17, 2008 Office Action issued in connection with U.S. Appl. No. 11/326,736.
Nov. 26, 2008 Office Action issued in connection with U.S. Appl. No. 11/169,875.
Holden et al. (2002) "Plasticity Time for A Reappraisal?" Science 296:2126-2129.
Poulsom et al. (2003) "Bone Marrow Stem Cells Contribute to Healing of the Kidney," J. Am. Soc. Nephrol. 14: s48-s54.
Feb. 27, 2009 European Examination Report issued in connection with European Application No. 04723937.1.
Apr. 28, 2009 Final Office Action issued in connection with U.S. Appl. No. 10/813,747.
Yang XB, et al. (2006), "Evaluation of Human Bone Marrow Stromal Cell Growth on Biodegradable Polymer/Bioglass Composites," Biochem Biophys Res Commun 342:1098-1107.
Fujii, S. et al. (2008), "Investigating a Clonal Human Periodontal Ligament Progenitor/Stem Cell Line In Vitro and In Vivo," J. Cell. Physiol. 215:743-749.
Neuhaus T. et al. (2003) "Stromal cell-derived factor 1alpha (SDF-1alpha) induces gene-expression of early growth response-1 . . . " Cell Proliferation. 36:75-86.
Salcedo R. et al. (1999) "Vascular endothelial growth factor and basic fibroblast growth factor induce expression of CXCR4 . . . " American Journal of Pathology. 154:1125-1135.
Examination report issued Oct. 10, 2009 in connection with European Application No. 05754008.0.
Final Office Action issued Oct. 8, 2009 in connection with U.S. Appl. No. 11/326,736.
Notice of Allowance issued Oct. 29, 2009 in connection with U.S. Appl. No. 10/813,747.
Final Office Action issued Dec. 9, 2009 in connection with U.S. Appl. No. 11/169,875.

(56) References Cited

OTHER PUBLICATIONS

Office Action issued Jan. 19, 2010 in connection with corresponding Japanese Application No. 2006-503989.

Kanbe K. et al. (2002) "Stimulation of Matrix Matalloprotease 3 Release from Human Chondrocytes by the Interaction of Stromal Cell-Derived Factor 1 and CXC Chemokine Receptor 4" Arthritis & Rheumatism 46:130-137.

Final Office Action issued Jun. 23, 2009 in connection with U.S. Appl. No. 11/169,875.

Final Office Action issued Jun. 2, 2010 in connection with U.S. Appl. No. 11/169,875.

Office Action issued Nov. 8, 2010 in connection with U.S. Appl. No. 12/660,003.

Office Action issued Jan. 24, 2011 in connection with U.S. Appl. No. 12/660,003.

Final Office Action issued Jul. 16, 2009 in connection with U.S. Appl. No. 10/955,709.

Final Office Action issued Jun. 22, 2009 in connection with U.S. Appl. No. 10/551,162.

Office Action Issued Aug. 26, 2010 in connection with U.S. Appl. No. 10/551,162.

Notice of Allowance issue Jan. 14, 2011 in connection with U.S. Appl. No. 10/551,162.

Office Action issued May 24, 2011 in connection with U.S. Appl. No. 11/326,736.

Office Action issued Sep. 22, 2009 in connection with U.S. Appl. No. 11/663,570.

Office Action issued Mar. 16, 2010 in connection with U.S. Appl. No. 11/663,570.

Communication Pursuant to Art. 94(3) EPC issued Apr. 16, 2010 in connection with European Application No. 05787106.3.

Communication Pursuant to Article 94(3) EPC issued Sep. 10, 2012 in connection with European Patent Application No. 04723937.1.

Office Action issued Jul. 18, 2011 in connection with U.S. Appl. No. 11/169,875.

Notice of Allowance issued Dec. 16, 2011 in connection with U.S. Appl. No. 11/169,875.

Notice of Allowance issued Jul. 6, 2011 in connection with U.S. Appl. No. 12/660,003.

Office Action issued Dec. 30, 2011 in connection with U.S. Appl. No. 11/326,736.

Examiner Interview Summary issued Jun. 26, 2012 in connection with U.S. Appl. No. 11/326,736.

Office Action issued Sep. 22, 2011 in connection with U.S. Appl. No. 12/924,008.

Office Action issued Mar. 21, 2012 in connection with U.S. Appl. No. 12/924,008.

Office Action issued Sep. 22, 2011 in connection with U.S. Appl. No. 11/663,563.

Office Action issued Apr. 4, 2012 in connection with U.S. Appl. No. 11/663,563.

Notice of Reasons for Rejection issued Feb. 7, 2012 in connection with Japanese Patent Application No. 2006-503990.

Medicina, vol. 39, No. 9, pp. 1569-1574 (2002).

Respiration and Circulation, vol. 50, No. 4, pp. 349-355 (2002).

Annual Review Blood 2003, pp. 1-10 (Jan. 2003).

English Language Translation of Apr. 16, 2013 Decision of Rejection issued in connection with Japanese Patent Application No. 2006/503990.

Jun. 29, 2012 Response and Request for Continued Examination, filed in connection with U.S. Appl. No. 10/551,326.

Feb. 27, 2013 Office Action, issued in connection with U.S. Appl. No. 11/326,736.

Apr. 23, 2012 Response, filed in connection with U.S. Appl. No. 12/924,008.

Sep. 12, 2012 Office Action, issued in connection with U.S. Appl. No. 12/924,008.

Feb. 1, 2013 Office Action, issued in connection with U.S. Appl. No. 12/924,008.

Jun. 28, 2013 Response, filed in connection with U.S. Appl. No. 12/924,008.

Oct. 4, 2012 Response, filed in connection with U.S. Appl. No. 11/663,563.

Dec. 27, 2009 Office Action, issued in connection with U.S. Appl. No. 11/663,563.

Dec. 22, 2009 Response, filed in connection with U.S. Appl. No. 11/663,570.

Mar. 16, 2010 Office Action, issued in connection with U.S. Appl. No. 11/663,570.

\* cited by examiner

PANEL 1

PANEL 2

PANEL 3

PANEL 4

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
ctatggagag gacgccacgc ctgg                                          24

<210> SEQ ID NO 2
<211> LENGTH: 23
```

```
<212> TYPE: DNA
<213> ORGANISM: Artificial Sequence
<220> FEATURE:
<223> OTHER INFORMATION: Primer

<400> SEQUENCE: 2
catagccatc gtagccttgt cct                                            23

<210> SEQ ID NO 3
<211> LENGTH: 16
<212> TYPE: DNA
<213> ORGANISM: Artificial Sequence
<220> FEATURE:
<223> OTHER INFORMATION: Primer

<400> SEQUENCE: 3
catgagagcc ctcaca                                                    16

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
agagcgacac cctagac                                                   17

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
agccgcatct tcttttgcgt c                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcatatttgg caggtttttc t                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cactgacacg ttggcagtgg                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
```

-continued catggagaag gctggggctc                                          20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atgcattggg aaccctgtgc                                          20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcacccaggg ctgaggtcca                                          20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gtggacgagg caagagtttc a                                        21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tggcaggtag gtgtggtagt g                                        21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
atgagagccc tcacactcct c                                        21

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
cgtagaagcg ccgataggc                                           19

<210> SEQ ID NO 15
<211> LENGTH: 21
<212> TYPE: DNA
<213> ORGANISM: Artificial Sequence

```
<220> FEATURE:
<223> OTHER INFORMATION: Primer

<400> SEQUENCE: 15
ctgttgccag agatggaggt t                                             21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcatcgctca ggaggtcctt                                               20

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ggcagcgttg gaacagaggt tgga                                          24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctctaaactg gagtggtcag ggct                                          24

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gacttctcag aaggcagag                                                19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ctatcctcca agtcccagag                                               20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aatgtctcca gcaccttcgt                                               20
```

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
agcggatgtg gtaaggcata                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ggcacaaaga agccgtactc                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cactgggcag acagtcagaa                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
agccagggtt gccaggacca                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ttttcccact ccaggagggc                                               20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ctctgcctgt ttggactttg t                                             21

<210> SEQ ID NO 28
<211> LENGTH: 21
<212> TYPE: DNA
<213> ORGANISM: Artificial Sequence
<220> FEATURE:
<223> OTHER INFORMATION: Primer

```
<400> SEQUENCE: 28
cctttgcttg ccttttacct c                                                  21

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
ccagtcagag gcagtacatg ctaagaattg agtta                                   35

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
gttttccatg gttttgtccc gcagta                                             26
```

PERIVASCULAR MESENCHYMAL PRECURSOR CELL INDUCED BLOOD VESSEL FORMATION

This application is a §371 National Stage of PCT International Application No. PCT/AU2004/000417, filed Mar. 29, 2004, claiming priority of Australian Provisional Application No. 2003901668, filed Mar. 28, 2003, the contents of all of which are hereby incorporated by reference.

FIELD OF THE INVENTION

This invention relates to mesenchymal precursor cells that carry a perivascular marker and are able to induced blood vessel formation, to a composition comprising such precursor cells and a method of inducing blood vessels. The invention also relates to treatment of cardiovascular conditions in particular ischemia.

BACKGROUND OF THE INVENTION

Vascular conditions constitute a major health problem, particularly in western countries. Vascular conditions include heart conditions, peripheral vascular disease and cerebrospinal vascular conditions.

A major proportion of these conditions result from a lack of supply of blood to the respective tissues which thus are either chronically or acutely deprived of necessary levels of oxygen and nutrients. Typically these conditions result in ischemias where there has been blockage of the blood vessel by build up of, for example, plaque or physical blood vessel damage such that these are either blocked or constricted.

Heart conditions are perceived as the most prominent vascular disease. About 11 million adults in the United States of America (1995) had coronary heart disease, that however is out of a total of about 60 million adults with cardiovascular disease. Other vascular conditions thus affect a greater number of adults.

A relatively common cerebrovascular condition can manifest as a stroke, where an occlusion can lead to an acute attack. A gradual diminution of supply may also lead to decreased capacity of the brain to function and it has been postulated that such conditions may be associated with the onset of certain dementias.

Peripheral vascular disease are associated with a number of conditions, for example, as a complication of diabetes where a typical inadequacy of the microcirculation depletes supply to the extremities particularly the feet and legs of oxygen and nutrients.

Another example of reduced localized supply can occur with the treatment of various wounds including severe burns or chronic wounds such as bed sores. Chronic wounds are difficult to heal, partly due to an insufficient vascular bed supply of nutrient and healing compounds.

Scar formation may also be exacerbated because the healing process often involves a highly fibrotic tissue forming within minimal blood vessel formation. Scar formation is also a difficulty associated with achieving an adequate vascular supply in circumstances where a prosthesis or other implant is surgically position in a human tissue. An inadequate blood supply to the interface between the implant and the surrounding tissue can lead to medical complications and necrosis. This is of far more noticeable relevance where the implant is intended as a long term slow release depot of for example a pharmaceutical.

Treatment of myocardial ischemias are probably the most advanced of current treatments of vascular conditions. Present treatments include pharmacological therapies, coronary artery bypass surgery and percutaneous revascularization using techniques such as balloon angioplasty. Standard pharmacological therapy to aims either increase blood supply to the heart muscle or decreasing the demand of the heart muscle for oxygen and nutrients. Increased blood supply to the myocardium by relaxation of smooth muscle is achieved by administering agents such as calcium channel blockers or nitroglycerin. Decreased demand of the heart muscle for oxygen and nutrients is accomplished either by agents that decrease the hemodynamic load on the heart, such as arterial vasodilators, or those that decrease the contractile response of the heart to a given hemodynamic load, such as β-adrenergic receptor antagonists. Surgical treatment of ischemic heart disease is based on the bypass of diseased arterial segments with strategically placed bypass grafts. Percutaneous neovascularization is based on the use of catheters to reduce the narrowing in diseased coronary arteries. All of these strategies are used to decrease the number of, or to eradicate, ischemic episodes, but all have various limitations, and particularly the pharmaceutical approach can have severe side effects.

Preliminary reports describe new vessel development in the heart through the direct injection of angiogenic proteins or peptides. The several members of the fibroblast growth factor (FGF) family (namely acidic fibroblast growth factor, aFGF; basic fibroblast growth factor, bFGF; fibroblast growth factor-5, FGF-5 and others) have been implicated in the regulation of angiogenesis during growth and development. Gene therapy has been suggested by Hammond et al in U.S. Pat. No. 5,792,453 as a delivery mechanism for these angiogenic compounds.

Another suggested approach to promoting new blood vessel formation for treatment of vascular conditions is the administration of stem cells which can differentiate and give rise to cells required for such blood vessels to form. One problem associated with this approach is that it is not entirely clear which progenitor cells are responsible for formation of blood vessel, or whether indeed more than one cell type is required or whether other angiogenesis promoters are required.

One reported approach described in U.S. Pat. No. 5,980,887 (to Isner et al) has resulted from the isolation of an endothelial progenitor cell and the discovery that such cells play a role in blood vessel formation.

Numerous attempts at isolating and enriching mesenchymal precursor cells have been made because of the potential that these cells have for medicinal use. Pittinger et al., (1999) show the expansion of clonogenic cells from bone marrow and describes a preparation of enlarged mesenchymal stem cells. A more recent example of such a method providing for a relatively high yield from bone marrow is disclosed in publication WO01/04268 to Simmons et al. Neither of these reported mesenchymal cells were indicated as being capable of regeneration vascular lineages of cells capable of leading to blood vessel formation.

To date however there have been no examples of isolated mesenchymal precursor cells capable of forming vascular tissues in vivo.

SUMMARY OF THE INVENTION

The present invention arises from the finding that a population of mesenchmal precursor cells (MPCs) is present in a perivascular niche. This has led to the demonstration that there is a much wider range of tissue type sources of MPCs than the single tissue, bone marrow, referred to in WO01/

04268. The present invention arises from the additional finding that an enriched population MPCs can be differentiated into two populations discriminated by the marker 3G5. MPCs that are 3G5 positive are considered of interest particularly for neovascularization applications, although demonstrably they are also able to differentiate into other tissue types. It is an additional finding of the present invention that levels of MPCs present in preferred enriched populations of this invention are able to give rise to sufficient numbers of committed cells to provide a number of differentiated tissue types. It is an additional finding of the present invention that certain levels of MPCs are useful on introduction into a patient to provide a measurable vascularisation benefit. It has thus specifically been found that a level of an estimated about $10^5$ MPCs are sufficient to provide a measurable benefit of cardiac improvement in an ischemic rat myocardium. This then provides a datum from which an assessment can bemade about the numbers of MPCs required to provide a beneficial effect. This is also believed to be the first time that a cardiac benefit has been shown on administration of a mesenchymal precursor cell to the heart.

In a first form of a first aspect the invention might be said to reside in a method of inducing the formation or repair of blood vessels in a target tissue of a patient, the method comprising the steps of administering to said patient an effective amount of a population of enriched perivascular mesenchymal precursor cells (MPCs) to induce new blood vessel formation in target tissue.

In a first form of a second aspect the invention might be said to reside in a method of repairing damaged tissue in a human subject in need of such repair, the method comprising:
(a) obtaining an enriched population of MPC, and
(b) contacting an effective amount of the enriched population of MPC with the damaged tissue of said subject In a first form of a third aspect the invention might be said to reside in a method of repairing damaged tissue in a human subject in need of such repair, the method comprising:
(a) expanding the enriched MPC of claim 41 in culture, and
(b) contacting an effective amount of the expanded cells with the damaged tissue of said subject.

In a first form of a fourth aspect the invention might be said to reside in a method of inducing formation or repair of blood vessels, the method comprising the steps of providing a population of enriched perivascular mesenchymal precursor cells (MPCs), contacting said cells with a growth media, and culturing said cells under conditions to induce them to differentiate into new blood vessels.

In a first form of a fifth aspect the invention might be said to reside in a composition for use in inducing heart vessel formation comprising a population of mesenchymal precursor cells (MCPs) in a pharmaceuticaly acceptable carrier, said MPCs carrying a perivascular marker and being a vascular progenitor.

Figure 1:
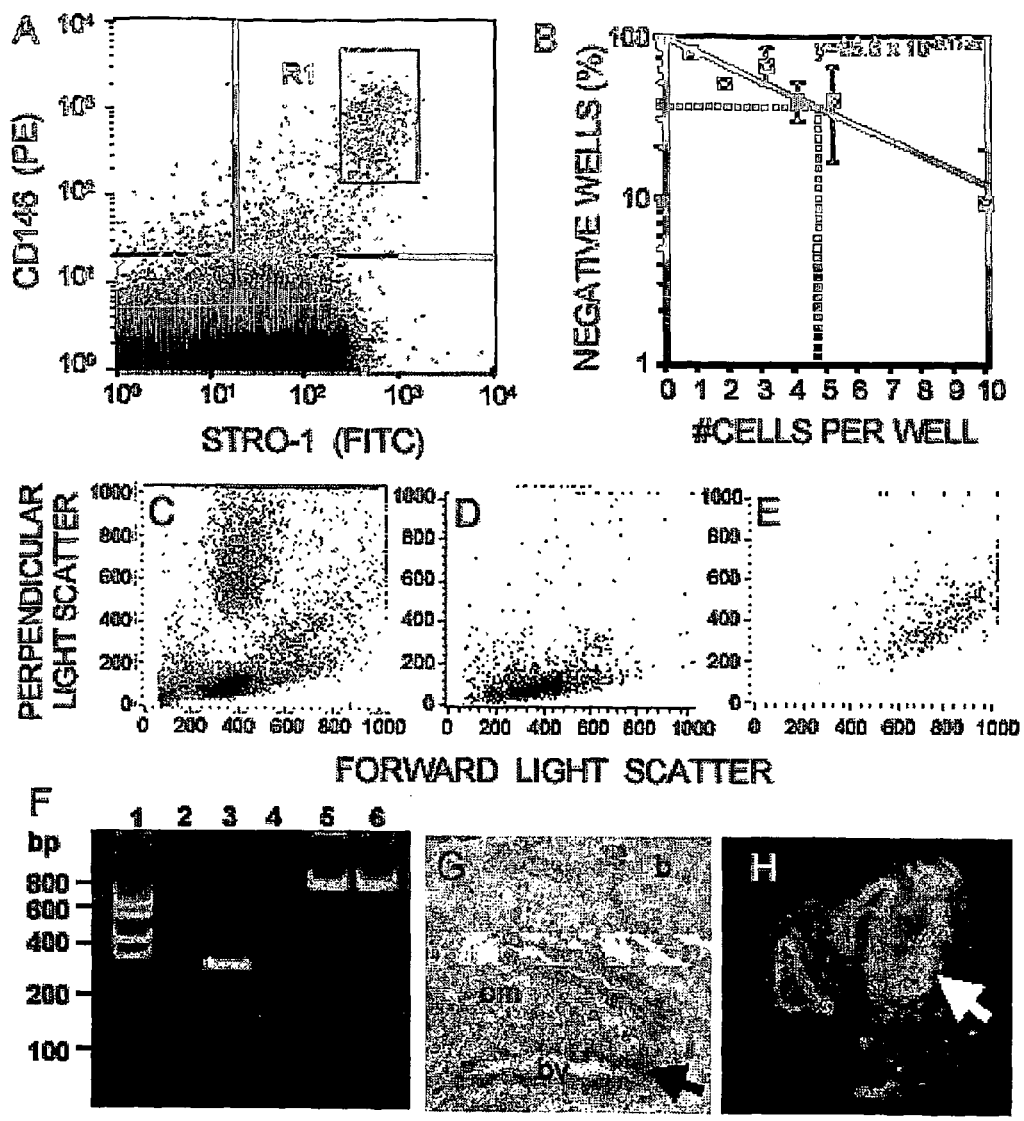
FIG. 1. Properties of STRO-1+ MACS-isolated cells co-labeled with anti-CD146 (CC9). (A) Sort region, R1, represents the double positive STRO-1$^{BRT}$/CD146+ population. (B) The incidence of clonogenic cell colonies (>50 cells) based on STRO-1$^{BRT}$/CD146+ expression was determined by limiting dilution analysis of 24 replicates per cell concentration using Poisson distribution analysis from 5 independent experiments. Forward (size) and perpendicular (granularity) light scatter characteristics of BMMNCs (C), STRO-1$^{int}$/CD146− cells (D) and STRO-1$^{BRT}$/CD146+ cells (E). (F) RT-PCR analysis of STRO-1$^{BRT}$/CD146+ sorted marrow cells for CBFA1 (lane 2), osteocalcin (lane 4) and GAPDH (lane 6) transcripts. Control cells (BMSSC cultures grown in the presence of dexamethasone) expressing CBFA1 (lane 1), osteocalcin (lane3), and GAPDH (lane 5) is also shown. Reaction mixes were subjected to electrophoresis on a 1.5% agarose gel and visualised by ethidium bromide staining. (G) In situ expression of CD146 on blood vessel (bv) walls (arrow) in human bone marrow (bm) sections near the bone (b) surface 20×. Sections were counter stained with Hematoxylin. (H) Dual Immunofluorescence staining demonstrating reactivity of the STRO-1 antibody labeled with Texas red and the CC9 antibody labeled with fluorescein isothiocyanate, reacting to blood vessel walls in frozen sections of human bone marrow.

DETAILED DESCRIPTION OF THE ILLUSTRATED AND EXEMPLIED EMBODIMENTS OF THE INVENTION

The invention resides in a method of inducing neovascularlisation by use of a composition of precursor cells. This has a range of application.

The invention thus has application in inducing blood vessel repair or formation, for example in the treatment of cerebrovascular ischemia, renal ischemia, pulmonary ischemia, limb ischemia, ischemic cardiomyopathy and myocardial ischemia, endothelial progenitor cells are administered.

A wide range of tissues might be treated and such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia.

The treatment of these conditions might include the step of isolating mesenchymal progenitor cells from a tissue of the patient, and then readministering them to the patient. The patient may also be treated with compound known to promote formation or repair of blood vessels or to enchance mesenchymal cell growth and/or vascular differentiation. For this purpose the MPCs may be administered to the patient by any suitable means, including, for example, intravensou infusion, bolus injection, and site directed delivery via a catheter.

The invention may also have applicability for the treatment of burns and wounds, including chronic sores such as bed sores, and certain ulcerations. For these conditions the MPCs might be applied topically, perhaps suspended in a cream or together with a suitable agent to assist with migration of the cells into the subsurface. Alternatively the MPCs might be held within a bandage perhaps within a protective matrix that is soluble on prolonged contact with the wound or other surface.

The invention may also have application where a reduced blood supply leads to for example baldness. The composition of MPCs may in injected subcutaneously or dermally in the affected area.

In vitro grown grafts of vascularised tissue are also contemplated by the invention whereby MPCs are grown in media and in the presence of compounds known to promote differentiation into vascular cells, to produce a graft which includes undifferentiation, partially differentiated and some differentiated cells.

In the case of an implant the surgeon may apply a composition containing the MPCs during the implantation a prosthesis, to promote vascularisation at the interface of the prosthesis and the surrounding tissue. An alternative process may be to have MPCs or a partially or fully differentiated graft developed on the implant. This may or may not be held within a protective matrix. The benefit of a graft is that vascularisation, and thus the healing process may be speeded up.

Blood vessels are an ideal position from which to delivery a medicinal product. The discovery of these MPCs and their properties of forming new blood vessels provides an opportunity to delivery over an extended period medicinal products.

The MPCs may be modified to carry various genetic material. The genetic material may be those that encode a variety of proteins including anticancer agents, hormones such as for example insulin, growth factors enzymes cytokines, and the like.

Alternatively the MPCs might be modified to express a blood vessel formation promoter which might assist in the MPCs induction of blood vessel formation, and assisting further with the maintenance of a good vascularisation of the tissue concerned.

For purposes of treating a cardiac vascular disease MPCs may be delivered to the myocardium by direct intracoronary (or graft vessel) injection using standard percutaneous catheter based methods under fluoroscopic guidance, at an amount sufficient for effective therapy. This may be in the range of between $10^4$ to $10^7$ MPCs. The injection should be made deeply into the lumen (about 1 cm within the arterial lumen) of the coronary arteries (or graft vessel), and preferably be made in both coronary arteries. By injecting the material directly into the lumen of the coronary artery by coronary catheters, it is possible to target MPC rather effectively, and to minimize loss during injection. Any variety of coronary catheter perfusion catheter can be used.

For the treatment of peripheral vascular disease, a disease characterized by insufficient blood supply to the legs an MPC may delivered by a catheter that will be inserted into the proximal portion of the femoral artery or arteries, thereby effecting migration of the MPCs to the capillaries of the skeletal muscles receiving blood flow from the femoral arteries. This will provide an angiogenic stimulus that will result in neovascularisation and or repair of blood vessels in skeletal muscle of the legs.

Compositions or products of the invention for use with coronary or peripheral vascular disease may conveniently be provided in the form of formulations suitable for intracoronary administration. A suitable administration format may best be determined by a medical practitioner for each patient individually. Suitable pharmaceutically acceptable carriers and their formulation are described in standard formulations treatises, e.g., Remington's Pharmaceuticals Sciences by E. W. Martin. Compositions may be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions may also be prepared to enhance shelf life and stability. The therapeutically useful compositions of the invention are prepared by mixing the ingredients following generally accepted procedures. For example, the selected components may be mixed to produce a concentrated mixture which may then be adjusted to the final concentration and viscosity by the addition of water and/or a buffer to control pH or an additional solute to control tonicity.

For use by the physician, the compositions will be provided in dosage form containing an amount of MPC composition which will be effective in one or multiple doses to induce angiogenesis at a selected level. As will be recognized by those in the field, an effective amount of therapeutic agent will vary with many factors including the age and weight of the patient, the patient's physical condition, and the level of angiogenesis to be obtained, and other factors.

The effective does of the compounds of this invention will typically be in the range of at least about $10^4$ MPCs, preferably about $10^6$ MPCs, and more preferably about $10^7$ MPCs. As noted, the exact dose to be administered is determined by the attending clinician, but is preferably in 1 ml phosphate buffered saline.

The presently preferred mode of administration in the case of heart disease is by intracoronary injection to one or both coronary arteries (or to one or more saphenous vein or internal mammary artery grafts) using an appropriate coronary catheter. The presently preferred mode of administration in the case of peripheral vascular disease is by injection into the proximal portion of the femoral artery or arteries using an appropriate arterial catheter.

Preferably the MPCs are coadministered with a blood vessel promoting compound. These might include acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor, insulin like growth factor, erythropoietin, colony stimulating factor, macrophage-CSF, GM-CSF and nitric oxidesynthase.

To further enhance angiogenesis an endothelial progenitor cell modified to express an endothelial cell mitogen may be used. Additionally, an perivascular cell mitogen or a nucleic acid encoding an perivascular cell mitogen can further be administered.

The MPCs might also be injected intramuscularly adjacent a site of the damaged blood vessel.

Composition might include a topical application for wounds and thus may be incorporated into creams lotions and the like.

The MPCs can be delivered in a composition that takes the form of an injectable preparation containing pharmaceutically acceptable carrier such as saline, for example, as necessary. The preparation may require sterilisation and may include stabiliser to maintain a uniform distribution of cells. The final dose of MPCs is preferably in the range of about $10^4$-$10^7$ cells.

The present invention relates to mesenchmal precursor cells, in particular those that may be present in the perivascular compartment of vascularised tissue. Such mesenchymal cells may be identified by the presence of the 3G5 surface marker, and perhaps additionally or separately by other early developmental markers such as CD146 (MUC18), VCAM-1 and STRO-1.

Precursor cells are early cells that are substantially at a pre-expansion stage of development. These are cells that have yet to differentiate to fully committed cells, however they need not be stem cells in a strict sense, in that they are necessarily able to differentiate into all types of cells. Partially differentiated precursor cells have a benefit in that they have a greater proliferative potential than stem cells.

The present precursor cells are somewhat differentiated in that they are committed to mesenchymal tissue, as opposed, for example, to haemopoietic tissues. It is evident from the data produced that the MPCs that have been isolated lack markers associated with haemopoietic cells such as CD34, and additionally their differentiation potential does not extend to haemopoietic lines. Additionally they need not necessarily have the potential to differentiate into all mesenchymal cell type, rather, they may be able to differentiate into one, two three or more cell types.

It is anticipated that these precursor cell harvested from the tissues concerned may be useful for regenerating tissue for cells types from which they have been sourced. Thus precursor cells isolated from heart may be reintroduced to regenerate heart tissue, however their potential need not be so limited, precursor cells isolated from one tissue type might be useful for regenerating tissue in another tissue type. The microenvironment in which an undifferentiated cell finds itself is known to exert an influence on the route of differentiation and therefore the reintroduction need not necessarily be tissue specific.

The data presented show that MPCs have been harvested and then re-introduced to produce bone and bone marrow and dentin and pulp respectively, in addition aterioles, cord like structures, have been produced after ex vivo expansion of isolated MPCs.

It is anticipated that a wide range of cells might be produced based on gene expression of markers characteristic for certain cell types. It is thus anticipated that under appropriate culture conditions the range of cell types that can be generated from the perivascular MPCs of the present invention include but are not limited to the following, osteoblast, odontoblast, dentin-producing, chondrocyte, tendon, ligament, cartilage, adipocyte, fibroblast, marrow stroma, osteoclast- and hematopoietic-supportive stroma, cardiac muscle, smooth muscle, skeletal muscle, pericyte, vascular, epithelial, glial, neuronal, astrocyte or oligodendrocyte cell.

One of the benefits of the finding that MPCs can be isolated from perivascular cells is that this greatly expands the range of source tissues from which MPCs can be isolated or enriched and there is no longer an effective restriction on the source of MPCs to bone marrow. The tissues from which these MPCs have been isolated in the exemplifications of this invention are human bone marrow, dental pulp cells, adipose tissue and skin. In addition in situ staining and histological studies have identified that MPC are present in the perivascular compartment of spleen, pancreas, brain, kidney, liver and heart. Given this wide and diverse range of tissue types where perivascular MPCs are present, it is proposed that MPC will also be present from an even wider range of tissue which may include, adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle.

These precursor cells of the present invention are distinguished from other known MPCs in that they are positive for 3G5 or perhaps that they carry another perivascular markers. They can be isolated by enriching for an early developmental surface marker present on perivascular cells, in particular the presence of one or more of CD146(MUC18), VCAM-1 and alternatively or additionally high level expression of the marker recognised by the monoclonal antibody STRO-1. Alternatively or additionally enrichment may be carried out using 3G5.

Markers associated with perivascular cells may also be present on the MPCs, for example alpha smooth muscle actin (αSMA).

Other early developmental markers associated with MPCs may also be present. These may include but are not necessarily limited to the group consisting of THY-1, VCAM-1, ICAM-1, PECAM-1, CD49a/CD49b/CD29, CD49c/CD29, CD49d/CD29, CD29, CD61, integrin beta 5, 6-19, thrombomodulin, CD10, CD13, SCF, STRO-1bri, PDGF-R, EGF-R, IGF1-R, NGF-R, FGF-R, Leptin-R (STRO-2). Positive expression of one or more of these markers may be used in methods of enriching for MPCs from source tissue.

The MPCs of the present invention may also be characterised by the absence of markers present in differentiated tissue, and enrichment may be based on the absence of such markers.

Similarly it is preferred that the enriched cell populations are not of haemopoietic origin and thus it is preferred that these cells are not present. Markers characteristically identified as not present include but are not limited to CD34, CD45 and glycophorin A. Additional other markers for this purpose might include CD20 and CD19 (B lymphocyte markers), CD117 (c-kit oncoprotein) present on hemopoietic stem cells and angioblasts, CD14 (macrophage), CD3 and CD4 (T cells).

It may be desirable to use the relatively quiescent, directly enriched or isolated perivascular MCPs. Alternatively it has been discovered that expansion of the enriched population can be carried out and have the beneficial effect of resulting in much greater numbers of cells. The effect of expansion of the directly enriched pool of cells is, however, that some differentiation of the initial MCPs will occur. Expansion over a 5 week period might result in an increase of $10^3$ fold. Other periods might be chosen to expand the population to between $10^2$ to $10^5$ fold. This potential might be directed by culturing them is media containing cytokines and other factors directing the differentiation to a particular tissue type for example PDGF and VEGF forming smooth muscle alpha cords. These could then be introduce into a tissue with, for example, an insult to assist with repair. Alternatively it may be desired after expansion to re select cells on the basis of an early developmental marker, that might be STRO-1$^{bri}$ to increase the proportion of MPCs in the population.

It is found that an essentially pure population of MCPs is not necessary to provide for formation of differentiated cells to form desired tissue structures. The enriched population may have levels of MCPs of greater than about 0.001, 0.01, 0.02, 0.05, 0.1, 0.2, 0.5 or 1% or higher as a proportion of total cell numbers in the enriched population. This order of enrichment can be achieved by the use of a single marker for selection of the enriched MCP population. This is particularly so where the source tissue has an inherently high level of perivascular MCPs. It is found that considerably more 3G5 pos MCPs are present in certain tissue, for example dental pulp, than in bone marrow. Thus in bone marrow 3G5 positive MPCs constitute about 15% of MPC based on STR1$^{bri}$ colony forming cells, whereas in dental pulp that are found to constitue 65% and greater than 90% in fat and skin tissues. Expansion of the population and then re-enrichment using a single marker coung result in higher leves of MPCs, perhaps levels greaer than about 0.1, 0.5, 1, 2, 5 or 10%

Whilst it is considered desirable that a substantial proportion and preferably a majority of precursor cells are perivascular MPCs, it is not considered essential for certain forms of the invention for perivascular MPCs to be the sole precursor cell form. Other forms of precursors may also be present without unduly interfering with the capacity of the perivascular MPCs to undergo the desired differentiation. Such other forms may include haemopoietic precursors or non-perivascular MPCs, perhaps being negative for 3G5.

Certain forms of the present invention provide perivascular MPCs substantially free of endothelial cells. In that context substantially free might be considered to be less than about 5, 2, 1, or 0.1% endothelial cells. Alternatively the context might be an assessment that the enriched population is von Willebrand Factor negative.

It will be understood that recognition of cells carrying the cell surface markers that form the basis of the separation can be effected by a number of different methods, however, all of these methods rely upon binding a binding agent to the marker concerned followed by a separation of those that exhibit binding, being either high level binding, or low level binding or no binding. The most convenient binding agents are antibodies or antibody based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies may be attached to a solid support to allow for a crude separation. The separation techniques should maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS.

It is in the context of these methods that a cell be either negative or positive. The positive cells may either be low (lo) or a hi (bright) expresser depending on the degree to which the marker is present on the cell surface, the terms relate to intensity of fluoresence or other color used in the color sorting process of the cells. The distinction of lo and bri will be understood in the context of the marker used on a particular cell population being sorted.

The method of enriching for perivascular MPCs might include the step of making a first partially enriched pool of cells by enriching for the expression of a first of the markers, and then the step of enriching for expression of the second of the markers from the partially enriched pool of cells.

It is preferred that the method comprises a first step being a solid phase sorting step, based on recognition of one or more of the markers. The solid phase sorting step of the illustrated embodiment utilises MACS recognising high level expression of STRO-1. This then gives an enriched pool with greater numbers of cells than if a high accuracy sort was used as a first step. If for example FACS is used first, many of the precursor cells are rejected because of their association with other cells. A second sorting step can then follow using an accurate separation method. This second sorting step might involve the use of two or more markers. Thus in the illustrated embodiment two colour FACS is used to recognise high level expression of the antigen recognised by STRO-1 as wells as the expression of CD146. The windows used for sorting in the second step can be more advantageously adjusted because the starting population is already partially enriched.

The method of enriching for perivascular MPCs might also include the harvesting of a source of the stem cells before the first enrichment step using known techniques. Thus the tissue will be surgically removed. Cells comprising the source tissue will then be seprated into a so called single cells suspension. This separation may be achieved by physical and or enzymic means.

The preferred source of such perivascular MPCs is human, however, it is expected that the invention is also applicable to animals, and these might include agricultural animals such as cows, sheep, pigs and the like, domestic animals such as dogs, laboratory animals such as mice, rats, hamsters, and rabbits or animals that might be used for sport such as horses.

In a further form the invention might be said to reside a method of generation tissue in a mammal comprising the step of enriching a population of precursor cells as in the first aspect of the invention, and introducing the enriched population into the mammal, and allowing the enriched population to generate the tissue in the mammal.

Another potential use for enriched cells of the present invention is as a means of gene therapy, by the introduction of exogenous nucleic acids for expression of therapeutic substances in the tissue types concerned.

In the context of the present invention the term isolated cell may mean that perivascular MPCs comprise at least 30, 40, 50, 60, 70, 80, or 95% of total cells of the population in which they are present.

EXAMPLE 1

Isolation and Expansion of Precursor Cells

Stem cell niches identified in a number of different adult tissues including skin, hair follicles, bone marrow, intestine, brain, pancreas and more recently dental pulp, are often highly vascularized sites.[1] The maintenance and regulation of normally quiescent stem cell populations is tightly controlled by the local microenvironment according to the requirements of the host tissue.[2,3] Both the supportive connective tissues of bone marrow and dental pulp contain stromal stem cell populations with high proliferative potentials capable of regenerating their respective microenvironments with remarkable fidelity, including the surrounding mineralized structures of bone and dentin.[4,5] In the postnatal organism, bone marrow stroma exists as a loosely woven, highly vascularized tissue that supports and regulates hematopoiesis.[6-8] At a time when many tissues have lost or decreased their ability to regenerate, adult bone marrow retains a capacity for continuous renewal of haematopoietic parenchymal tissue and is responsible for remodeling the adjoining bone surfaces.[9,10] In contrast, the inner pulp chamber of teeth is comprised of a non-hematopoietic, compact fibrous tissue, infiltrated by a microvascular network, that is entombed by mineralized dentin.[11-13] Following tooth maturation, dental pulp becomes relatively static, acting only in a reparative capacity in response to a compromised dentin matrix caused by insults such as caries or mechanical trauma.

Precursors of functional osteoblasts (BMSSCs: bone marrow stromal stem cells) and odontoblasts (DPSCs: dental pulp stem cells), both forms of MPCs identified by their source tissue, were initially identified by their capacity to form clonogenic cell clusters in vitro, a common feature amongst different stem cell populations.[4,14-18] The progeny of ex vivo expanded BMSSCs and DPSCs share a similar gene expression profile for a variety of transcriptional regulators, extracellular matrix proteins, growth factors/receptors, cell adhesion molecules, and some, but not all lineage markers characteristic of fibroblasts, endothelial cells, smooth muscle cells and osteoblasts.[4,19] However, previous studies have documented that individual BMSSC colonies demonstrate marked differences in their proliferation rates in vitro and developmental potentials in vivo.[5,14,20] Similar to these findings, we have recently observed comparable levels of heterogeneity in the growth and developmental capacity of different DPSC colonies.[21] Together, these studies infer a hierarchical arrangement of stromal precursor cells residing in bone marrow and dental pulp, headed by a minor population of highly proliferative pluri-potential stem cells that give rise to committed bi- and uni-potential progenitor cell populations.[22]

Despite our extensive knowledge about the properties of cultured BMSSCs and DPSCs, we still do not know if their in vitro characteristics are an accurate portrait of their true gene expression patterns and developmental potentials in situ. In addition, it is not formally known if all of the colony-forming cells within each tissue are derived from one pluri-potent stem cell pool or whether they arise from committed progenitors belonging to distinct lineages. There is also a lack of information regarding the precise anatomical location of BMSSCs and DPSCs in their respective tissues. This is mainly attributed to the rarity of stem cells and the absence of specific markers that identify different developmental stages during osteogenesis and odontogenesis, particularly for primitive subpopulations. It has previously been hypothesized that one possible niche for precursors of osteoblasts and odontoblasts may be the microvasculature networks of bone marrow and dental pulp, respectively.[23,24]

Materials and Methods

Tissue Samples

Iliac crest-derived bone marrow mononuclear cells (BM-MNCs), from normal human adult volunteers were obtained under guidelines set by the Royal Adealaide Hospital Human Ethics Committee. Normal human impacted third molars were collected from young adults the University of Adelaide Dental Clinic Research under approved guidelines set by the University of Adelaide Human Ethics Committee, respectively. Discarded full thickness skin and peripheral adipose tissue were obtained from routine plastic surgery procedures from the Skin Cell Engineering Laboratory, under the guidelines set by the Royal Adelaide Hospital Human Ethics Committee. The pulp tissue was separated from the crown and root as previously described.[4] Single cell suspensions of dental pulp, skin and adipose tissue were prepared by enzymatic digestion in a solution of 3 mg/ml collagenase type I (Worthington Biochem, Freehold, N.J.) and 4 mg/ml dispase (Boehringer Mannheim, GMBH, Germany) for one to three hours at 37° C. Single cell suspensions were obtained by passing the cells through a 70 μm strainer (Falcon, BD Labware, Franklin Lakes, N.J.). Cell (0.01 to $1 \times 10^5$/well) preparations of bone marrow, dental pulp, skin and adipose were then used for either, immunolselection, RNA extraction, or direct culture in 6-well plates (Costar, Cambridge, Mass.) as described below.

Other human tissue specimens (Brain, liver, heart, kidney, lung, spleen, thymus, lymph node, pancreas, skin) were obtained from autopsies carried out at the Royal Adelaide Hospital during routine pathological examinations under approved guidelines set by the Royal Adelaide Hospital Human Ethics Committee. Small specimens approximately 0.5 $cm^2$ of each tissue type were placed into Tissue-Tek II cryomoulds 25 mm×20 mm×5 mm (Miles Laboratories; Naperville, Ill.) and embedded with O.C.T. compound medium (Miles Laboratories) by immersion into a 150 ml to 200 ml pyrex glass beaker of iso-pentane (BDH Chemicals, Poole, England) pre-cooled by suspending a glass beaker into a bath of liquid nitrogen. The isopentane has cooled when the bottom of the glass is white. The frozen sections were immediately stored at −80° C. Frozen sections of nerve and muscle tissue were obtained from the Histopathology Department of the I.M.V.S., South Australia and sections of foreskin were obtained from the Immunology Department of the I.M.V.S., South Australia. Sections of formalin fixed, paraffin embedded human foetal limb (52 days) were kindly provided by Dr. T. J. Khong from the Department of Histopathology, Women's and Children's Hospital, Adelaide, South Australia.

Colony Efficiency Assay and Culture

Single cell suspensions were plated at low plating densities (between 1,000 and 10,000 cells per well, as triplicates in six well plates) to assess colony-forming efficiency of different immunoselected cell fractions. The cells were cultured in alpha-Modification of Eagle's Medium supplemented with 20% foetal calf serum, 2 mM L-Glutamine, 100 µM L-ascorbate-2-phosphate, 100 U/ml penicillin and 100 µg/ml streptomycin at 37° C. in 5% $CO_2$. Day 14 cultures were fixed with 4% formalin, and then stained with 0.1% toluidine blue. Aggregates of equal to or greater than fifty cells were scored as clonogenic colonies equivalent to colony forming units-fibroblastic (CFU-F).

Magnetic-Activated Cell Sorting (MACS)

This procedure is a modification of that described elsewhere.[25] Briefly, approximately $1\times10^8$ BMMNCs were incubated with STRO-1bri supernatant (murine anti-human BMSSCs, IgM)[29] (1/2) for 1 hour on ice. The cells were then washed with PBS/5% FBS and resuspended in a 1/50 dilution of biotinylated goat anti-mouse IgM (µ-chain specific; Caltag Laboratories, Burlingame, Calif.) for 45 minutes on ice. After washing, the cells were incubated with streptavidin microbeads (Miltenyi Biotec, Bergisch Gladbach, F.R.G.) for 15 minutes on ice, then separated on a Mini MACS magnetic column (Miltenyi Biotec) according to the manufacturers recommendations.

Fluorescence Activated Cell Sorting (FACS)

STRO-1bri MACS isolated cells were incubated with a streptavidin-FITC conjugate (1/50; CALTAG Laboratories) for 20 minutes on ice then washed with PBS/5% FBS. Single-color fluorescence activated cell sorting (FACS) was performed using a FACStar$^{PLUS}$ flow cytometer (Becton Dickinson, Sunnyvale, Calif.). Dual color-FACS analysis was achieved by incubating MACS-isolated STRO-1$^{bri}$ BMMNCs with saturating (1:1) levels of CC9 antibody supernatant (mouse anti-human CD146/MUC-18/MelCAM, $IgG_{2a}$, Dr. Stan Gronthos) for one hour on ice. After washing with PBS/5% FBS, the cells were incubated with a second label goat anti-mouse $IgG_2$a (γ-chain specific) phycoerythrin (PE) conjugate antibody (1/50, CALTAG Laboratories) for 20 minutes on ice. The cells were then sorted using the automated cell deposition unit (ACDU) of a FACStar$^{PLUS}$ flow cytometer. Limiting dilution assay: seeded 1, 2, 3 4, 5, & 10 cells per well, 24 replicates, cultured in serum-deprived medium for 10 days as previously described (26). Similarly, freshly prepared unfractionated BMMNCs were incubated with CC9 ($IgG_{2a}$) and 3G5 (IgM) antibodies or isotype-matched negative control antibodies for one hour on ice. After washing with PBS/5% FBS, the cells were incubated with a second label goat anti-mouse $IgG_{2a}$ (γ-chain specific) phycoerythrin (PE) and IgM (1/50; CALTAG Laboratories) conjugated antibodies for 30 minutes on ice. Cells were washed in PBS/%5 FBS prior to being analysed using a FACStar$^{PLUS}$ flow cytometer. Positive reactivity for each antibody was defined as the level of fluorescence greater than 99% of the isotype matched control antibodies.

Flow Cytometric Analysis

Single cell suspensions of ex vivo expanded bone marrow MPC were prepared by trypsin/EDTA treatment then incubated with neat STRO-1 supernatant or antibodies identifying different cell lineage-associated markers (10 µg/ml) for one hour on ice. The cells were then washed in PBS/5% FBS then incubated either with a goat anti-murine IgM-phycoerythrin (1/50, SouthernBiotechnologies), goat anti-murine or anti-rabbit IgG-phycoerythrin (Caltag Laboratories). For those antibodies identifying intracellular antigens, cell preparations were permeabilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker with reference to the isotype matched negative control antibodies.

Immunhistochemistry

Human tissue sections (µm) were de-waxed in xylene and rehydrated through graded ethanol into PBS. Frozen tissue sections (µm) and cytospin preparations were fixed with cold acetone at −20° C. for 15 minutes then washed in PBS. The samples were subsequently treated with PBS containing 1.5% of hydrogen peroxide for 30 minutes, washed then blocked with 5% non-immune goat serum for 1 hour at room temperature. Samples were incubated with primary antibodies for 1 hour at room temperature. Antibodies used: Mouse ($IgG_1$ & $IgG_{2a}$) controls (Caltag, Burlingame, Calif.); Rabbit (Ig) control, 1A4 (anti-α smooth muscle actin, $IgG_1$), 2F11 (anti-neurofilament, $IgG_1$), F8/86 (murine anti-von Willebrand Factor, $IgG_1$) (Dako, Carpinteria, Calif.); STRO-1; CC9 (anti-CD146); LF-151 (rabbit anti-human dentinsialoprotein; Dr. L. Fisher, NIDCR/NIH, MD). Working dilutions: rabbit serum (1/500), monoclonal supernatants (1/2) and purified antibodies (10 µg/ml). Single staining was performed by incubating the samples with the appropriate secondary antibody, biotinylated goat anti-mouse IgM, $IgG_1$, $IgG_{2a}$ or biotinylated goat anti-rabbit for one hour at room temperature (Caltag Laboratories). Avidin-Peroxidase-complex and substrate were then added according to the manufacturer instructions (Vectastain ABC Kit standard, Vector Laboratories). Samples were counterstained with hematoxylin and mounted in aqueous media. Dual-fluorescence labeling was achieved by adding the secondary antibodies, goat anti-mouse IgM-Texas Red
and IgG-FITC (CALTAG Laboratories), for 45 minutes at room temperature. After washing the samples were mounted in VECTASHIELD fluorescence mountant.

Immunomagnetic Bead Selection

Single cell suspensions of dental pulp tissue were incubated with antibodies reactive to STRO-1 (1/2), CD146 (1/2), or 3G5 (1/2) for 1 hour on ice. The cells were washed twice with PBS/1% BSA then incubated with either sheep anti-mouse IgG-conjugated or rat anti-mouse IgM-congugated magnetic Dynabeads (4 beads per cell: Dynal, Oslo, Norway) for 40 minutes on a rotary mixer at 4° C. Cells binding to beads were removed using the MPC-1 magnetic particle concentrator (Dynal) following the manufactures recommended protocol.

Matrigel-Arteriole Assay

Single cell suspensions of ex vivo expanded bone marrow STRO-1$^{bright}$ MPC were prepared by trypsin/EDTA treatment then plated into 48-well plates containing 200 µl of matrigel. The STRO-1$^{bright}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed for alpha-smooth muscle actin identified with a goat-anti-murine IgG horse radish peroxidase antibody/Vectastaining Kit as described above.

Osteogenic, Adipogenic and Chondrogenic Differentiation of MPC In Vitro

Single cell suspensions of ex vivo expanded adipose-derived MPC were cultured in αMEM supplemented with 10% FCS, 100 µM L-ascorbate-2-phosphate, dexamethasone $10^{-7}$ M and 3 mM inorganic phosphate previously shown to induce bone marrow MPC to form a mineralized bone matrix in vitro (Gronthos et al., 2003). Mineral deposits were identified by positive von Kossa staining. Adipogenesis was induced in the presence of 0.5 mM methylisobutylmethylxanthine, 0.5 µM hydrocortisone, and 60 µM indomethacin as previously described (Gronthos et al. 2003). Oil Red O staining was used to identify lipid-laden fat cells. Chondrogenic differentiation was assessed in aggregate cultures treated with 10 ng/ml TGF-β3 as described (Pittenger et al., 1999)

In Vivo Transplantation Studies

Approximately $5.0 \times 10^6$ of ex vivo expanded cells derived from either STRO-1$^{bri}$/CD146$^+$ BMSSCs or CD146$^+$ DPSCs were mixed with 40 mg of hydroxyapatite/tricalcium phosphate (HA/TCP) ceramic powder (Zimmer Inc, Warsaw, Ind.) and then transplanted subcutaneously into the dorsal surface of 10-week-old immunocompromised beige mice (NIH-bg-nu-xid, Harlan Sprague Dawley, Indianapolis, Ind.) as previously described.[4] These procedures were performed in accordance to specifications of an approved animal protocol (NIDCR #00-113).

Reverse Transcription-Polymerase Chain Reaction.

Total RNA was prepared from STRO-1$^{BRT}$/CD146$^+$ sorted BMMNCs, and control cells (primary BMSSC cultures grown in the presence of $10^{-7}$ M dexamethasone for three weeks) using RNA STAT-60 (TEL-TEST Inc. Friendswood Tex.). First-strand cDNA synthesis was performed with a first-strand cDNA synthesis kit (GIBCO BRL, Life Technologies) using an oligo-dT primer. First strand cDNA (2 µl) was added to 46 µl of a 1×PCR master reaction mix (Roche Diagnostics, Gmbh Mannheim Germany) and 10 pMol of each human specific primer sets: CBFA1 (632 bp, and three smaller alternative splice variants)[27] sense 5'-CTATG-GAGAGGACGCCACGCCTGG-3' [SEQ ID NO. 1], antisense, 5'-CATAGCCATCGTAGCCTTGTCCT-3' [SEQ ID NO. 2]; osteocalcin (310 bp)(4) sense, 5'-CATGAGAGC-CCTCACA-3' [SEQ ID NO. 3], antisence, 5'-AGAGCGA-CACCCTAGAC-3' [SEQ ID NO. 4]; GAPDH (800 bp) (4) sense, 5'-AGCCGCATCTTCTTTTGCGTC-3' [SEQ ID NO. 5]; antisense 5'-TCATATTTGGCAGGTTTTTCT-3' [SEQ ID NO. 6]. The reactions were incubated in a PCR Express Hybaid thermal cycler (Hybaid, Franklin, Mass.) at 95° C. for 2 minutes for 1 cycle then 94° C./(30 sec), 60° C./(30 sec), 72° C./(45 sec) for 35 cycles, with a final 7 minute extension at 72° C. Following amplification, each reaction was analyzed by 1.5% agarose gel electrophoresis, and visualized by ethidium bromide staining.

Results

BMSSCs and DPSCs Express Vascular Associated Antigens STRO-1 and CD146 In Vivo.

We have previously demonstrated the efficacy of magnetic activated cell sorting (MACS), to isolate and enrich for all detectable clonogenic colonies from aspirates of human marrow, based on their high expression of STRO-1 antigen.[25-26]

To further characterize BMSSCs we incubated the STRO-1$^{bri}$ MACS isolated cells with another monoclonal antibody, CC9,[28] that recognizes the cell surface antigen CD146, also known as MUC-18, Mel-CAM and Sendo-1, that is present on endothelial and smooth muscle cells. These studies determined that CC9, selectively bound the STRO-1 bright expressing fraction (STRO-1$^{BRT}$) from the total STRO-1$^+$ population by dual-color FACS analysis (FIG. 1A). Cloning efficiency assays using Poisson distribution statistics, yielded a marked increase in the incidence of BMSSCs (1 colony per 5 STRO-1$^{BRT}$/CD146$^+$ cells plated), and achieved a $2 \times 10^3$ fold enrichment of the clonogenic colony population when compared to unfractionated marrow (FIG. 1B). No colony formation could be detected in STRO-1$^{BRT}$/CD146$^-$ cell fraction (data not shown).

The light scatter properties of STRO-1$^{BRT}$/CD146$^+$ marrow cells were typically larger and more granular than the nucleated erythroid cells and B-lymphocytes comprising the bulk of the STRO-1$^+$ population[29] (FIG. 1C-E). Cytospin preparations of STRO-1$^{BRT}$/CD146$^+$ sorted cells were found to be negative for the erytiroid (glycophorin-A) and leukocyte (CD45) associated markers (data not shown). Confirmation that BMSSCs represented an early osteogenic precursor population was obtained by RT-PCR analysis of highly purified MACS/FACS-isolated STRO-1$^{BRT}$/CD146$^+$ cells, which failed to detect the early and late osteogenic, markers CBFA1 and osteocalcin, respectively (FIG. 1F). However, the progeny of STRO-1$^{BRT}$/CD146$^+$ sorted BMSSCs were found to express both CBFA1 and osteocalcin, following ex vivo expansion. Immunolocalization studies demonstrated that the CD146 antigen was predominantly expressed on blood vessel walls in sections of human bone marrow (FIG. 1G). Localization of both STRO-1 and CD146 was confined to large blood vessels in frozen sections of human bone marrow trephine (FIG. 1H).

Figure 2:
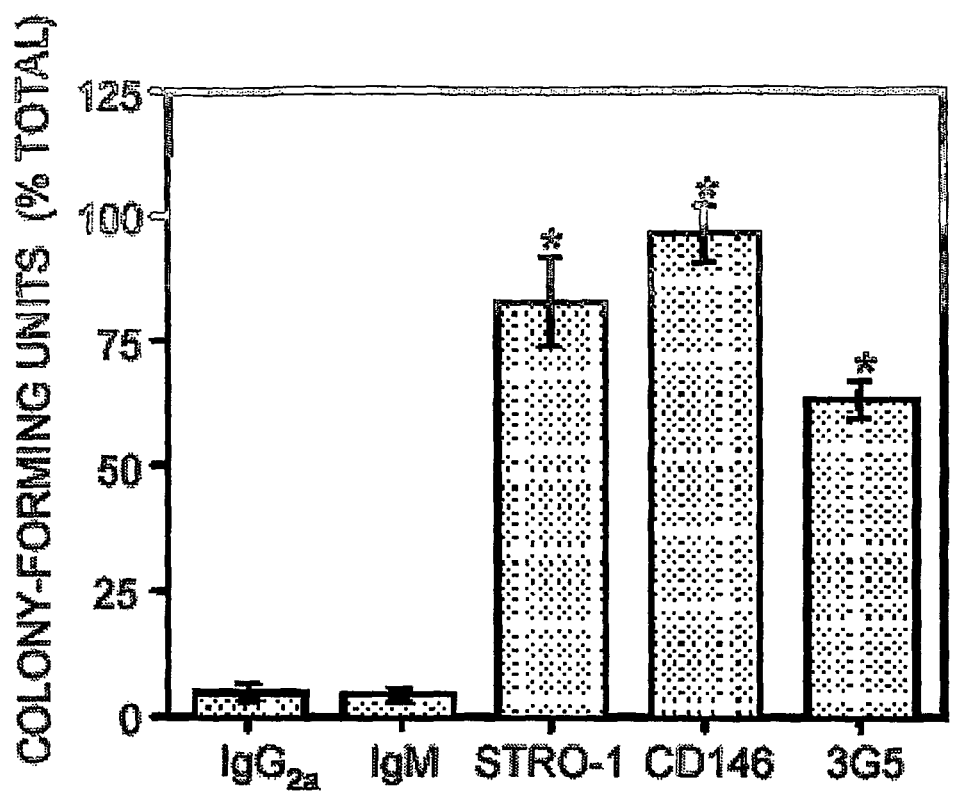
FIG. 2. Immunophenotypic analysis of DPSCs in vivo. The bar graph depicts the number of clonogenic colonies retrieved from single cell suspensions of dental pulp following immunomagnetic bead selection based on reactivity to antibodies that recognize STRO-1, CD146, and 3G5 and isotype-matched negative control antibodies. The data are expressed as the number of colony-forming units obtained in the bead positive cell fractions as a percentage of the total number of colonies in unfractionated pulp cells averaged from three separate experiments. Statistical significance (*) was determined using the student t-test (p 0.01) comparing the percent total number of colonies for each antibody with the corresponding isotype-matched control.

Immunoselection protocols were subsequently used to determine if human DPSCs also expressed STRO-1 and CD146 in situ. The use of either MACS or FACS analysis to isolate DPSCs was restrictive due to the rarity of these cells (1 colony-forming cell per $2 \times 10^3$ cells plated) compounded by the limited number of pulp cells (approximately $10^5$ cells per pulp sample) obtained following processing. To circumvent this, we pooled several pulp tissues obtained from 3 to 4 different third molars per experiment and employed immunomagnetic bead selection on single cell suspensions of pulp tissue, based on their expression of either the STRO-1 or CD146 antigens. The STRO-1$^+$ fraction represented approximately 6% of the total pulp cell population. Comparative studies demonstrated that growth rates of individual colonies were unperturbed in the presence of magnetic beads (data not shown). Colony efficiency assays indicated that the majority of dental pulp derived colony-forming cells (82%) were represented in the minor, STRO-1$^+$ cell fraction analogous to BMSSCs (FIG. 2). The mean incidence of DPSCs in the STRO-1 positive fraction (329 colony-forming cells per $10^5$ cells plated±56 SE, n=3) was six-fold greater than unfractionated pulp cells (55 colony-forming cells per $10^5$ cells plated±14 SE, n=3). Using a similar strategy, different fractions of human dental pulp cells were selected based on their reactivity with the antibody, CC9. Colony efficiency assays showed that a high proportion (96%) of dental pulp-derived clonogenic colonies were also present in the CD146$^+$ population, using immunomagnetic Dynal bead selection (FIG. 2). The mean incidence of clonogenic colonies in the CD146$^+$ fraction (296 colony-forming cells per $10^5$ cells plated±37

SE, n=3) was seven-fold greater than unfractionated pulp cells (42 colony-forming cells per $10^5$ cells plated±9 SE, n=3).

Figure 3:
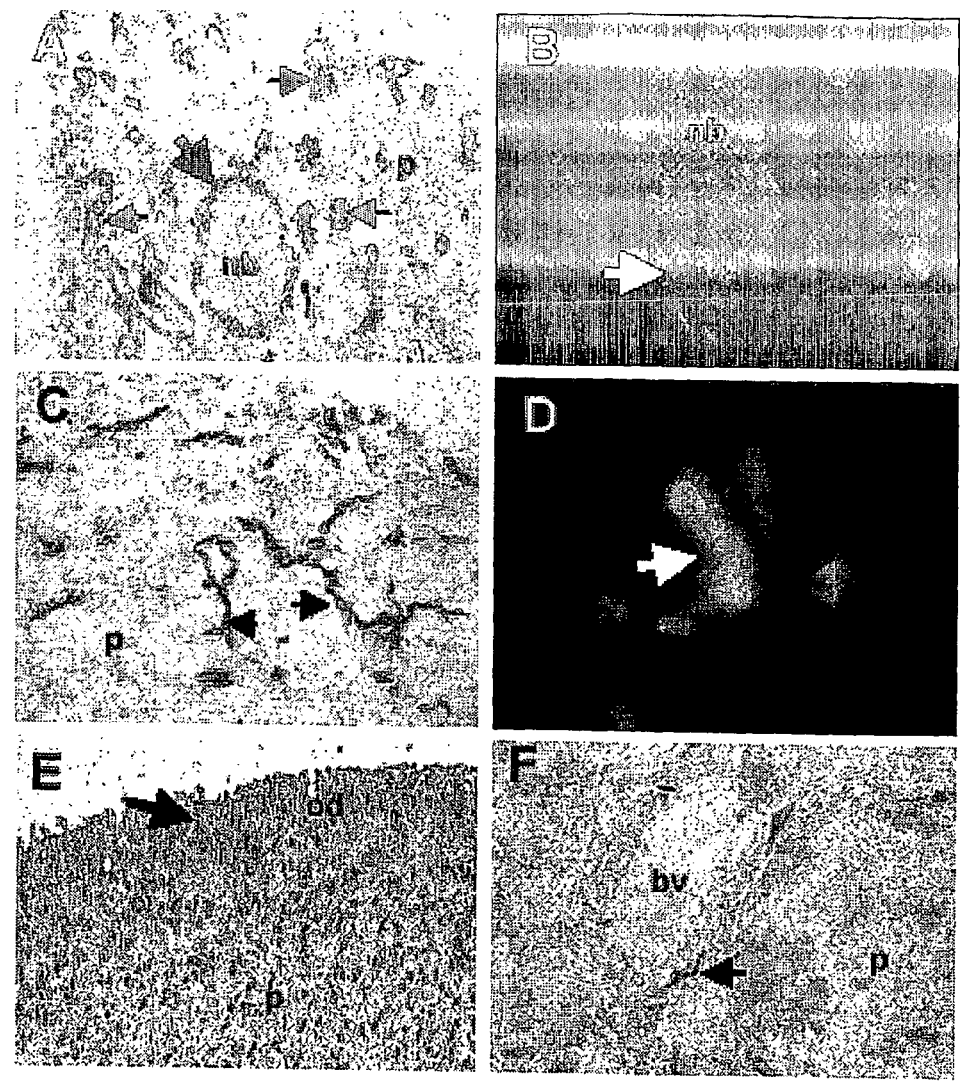
FIG. 3. Reactivity of perivascular makers in dental pulp. (A) Immunolocalization of the STRO-1 antigen on blood vessels (small arrows) in human dental pulp (p) and around perineurium (large arrow) surrounding a nerve bundle (nb) 20×. (B) Dual Immunofluorescence staining demonstrating reactivity of the STRO-1 antibody labeled with Texas Red to dental pulp perineurium (arrow) in combination with an anti-neurofilament antibody labeled with fluorescein isothiosyanate staining the inner nerve bundle (nb), 40×. (C) Immunolocalization of the CD146 antigen to blood vessel walls in human dental pulp tissue 20×. (D) Dual Immunofluorescence staining demonstrating reactivity of the STRO-1 antibody labeled with Texas red to a blood vessel and the CC9 antibody labeled with fluorescein isothiosyanate. (E) Immunohistochemical staining of pulp tissue with a rabbit polyclonal anti-DSP antibody (arrow) to the odontoblast outer layer (od). 20×. (F) 3G5 reactivity to a single pericyte (arrow) in a blood vessel (bv) wall 40×. Tissue sections were counter stained with Hematoxylin.

Immunolocalization studies showed that STRO-1 expression was restricted to blood vessel walls and perineurium surrounding the nerve bundles, but was not present in the mature odontoblast layer or fibrous tissue, in frozen sections of human dental pulp tissue (FIG. 3A-B). Furthermore, co-localization of CD146 with STRO-1 was detected on the outer blood vessel cell walls, with no reactivity to the surrounding fibrous tissue, odontoblast layer, and the perineurium of the nerve (FIG. 3C-D). Importantly, expression of human odontoblast-specific differentiation marker, dentin-sialoprotein (DSP), was restricted to the outer pulpal layer containing mature odontoblasts (FIG. 3E) and was absent in fibrous tissue, nerve bundles and blood vessels.

Differential Expression of the Perivascular Marker 3G5 by BMSSCs and DPSCs.

Figure 4:
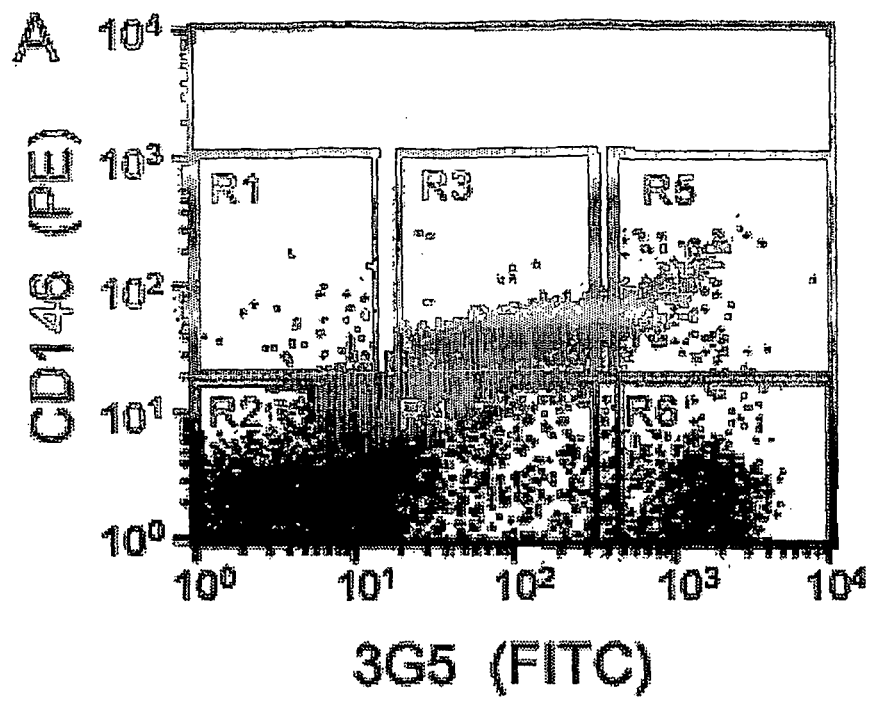
FIG. 4. 3G5 reactivity to BMSSCs. (A) The representative histogram depicts a typical dual-color FACS analysis profile of whole bone marrow mononuclear cells (BMMNCs) expressing CD146 (PE) and 3G5 (FITC). (B) Colony efficiency assays were performed for all the different expression patterns observed (regions "R" 1-6). The data are expressed as the mean incidence of colony-forming units for each cell fraction averaged from three separate experiments.

In the present study, flow cytometric analysis revealed that the cell surface antigen, 3G5, was highly expressed by a large proportion (54%) of hematopoietic marrow cells (FIG. 4A). This observation eliminated 3G5 as a candidate marker for isolating purified populations of BMSSCs directly from aspirates of human marrow. In addition, dual-FACS analysis based on 3G5 and STRO-1 expression was not possible since both antibodies shared the same isotype. Nevertheless, in vitro colony efficiency assays for different 3G5/CD146 FACS sorted subfractions demonstrated that only a minor proportion (14%) of bone marrow clonogenic colonies expressed the 3G5 antigen at low levels (FIG. 4B). Conversely, a larger proportion (63%) of clonogenic DPSCs (192 colony-forming cells per $10^5$ cells plated±18.4 SE n=3) were present in the 3G5$^+$ cell fraction following immunomagnetic bead selection (FIG. 2). 3G5 demonstrated specific reactivity to pericytes in frozen sections of human dental pulp tissue (FIG. 3F).

Figure 5:
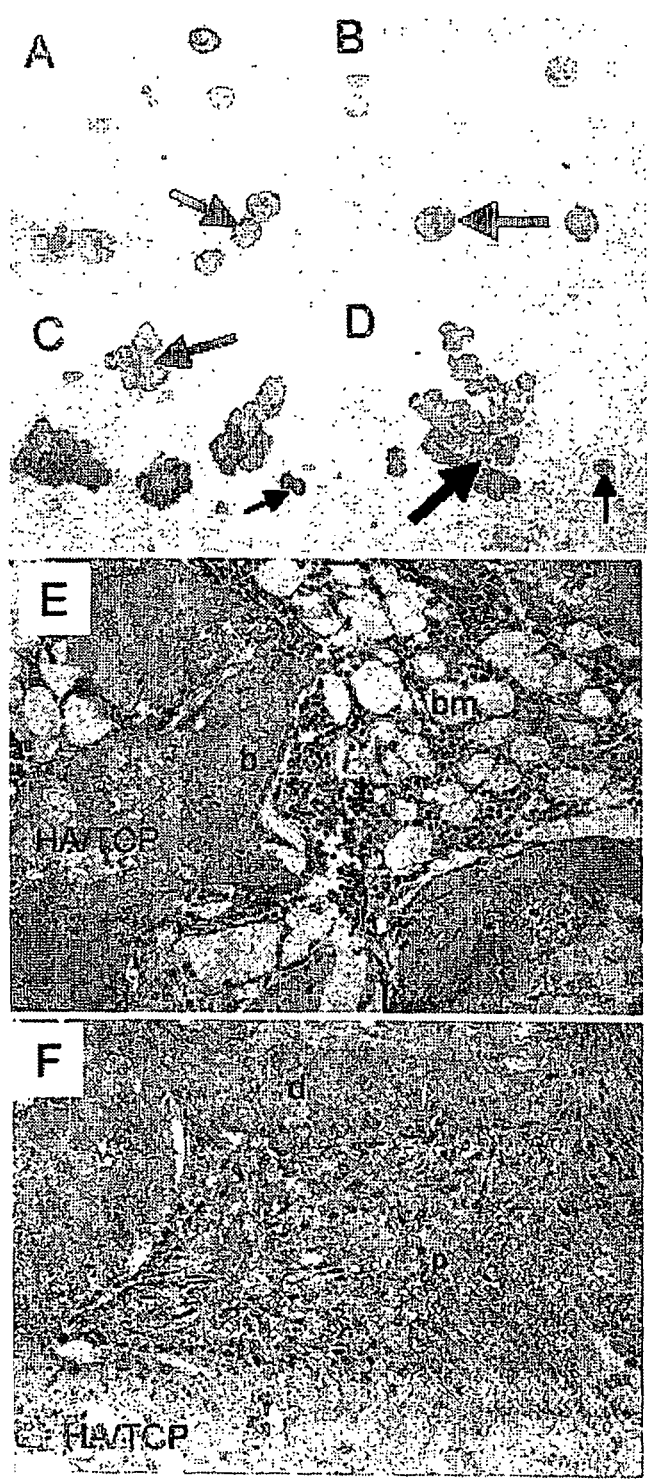
FIG. 5. Developmental potential of purified BMSSCs and DPSCs in vivo. Cytospin preparations of MACS/FACS isolated STRO-1$^{BRT}$/CD146 marrow cells (arrow) stained with an antibody specific to α-smooth muscle actin (A) and von Willebrand Factor (B). CD146+ pulp cells (large arrow) isolated by immunomagnetic bead selection (magnetic beads depicted by small arrows), stained with an antibody specific to α-smooth muscle actin (C) and von Willebrand Factor. (D). (E) Ectopic bone formation (b) and haematopoietic/adipogenic marrow (bm) by ex vivo expanded cells derived from STRO-1$^{BRT}$/CD146+ BMSSCs transplanted with HA/TCP into immunocompromised mice for three months (E). (F) Ectopic formation of dentin (d) and fibrous pulp tissue (p) by ex vivo expanded cells derived from CD146+ DPSCs transplanted with HA/TCP into immunocompromised mice for three months. Sections were stained with Hematoxylin & Eosin.

We next analyzed the expression of more specific markers of endothelial cells (von Willebrand Factor) and smooth muscle cells/pericytes (α-smooth muscle actin) on cytospin preparations using freshly isolated SRO-1$^{BRT}$/CD146$^+$ BMSSCs and CD146$^+$ expressing DPSCs. A large proportion of purified BMSSCs (67%), were found to be positive for α-smooth muscle actin (FIG. 5A), but lacked expression of von Willebrand Factor (FIG. 5B). Similarly, the majority of isolated DPSCs (85%) were also found to express α-smooth muscle actin, but not von Willebrand Factor (FIG. 5C, 5D). Purified populations of STRO-1$^{BRT}$/CD146$^+$ BMSSCs and CD146$^+$ DPSCs were subsequently expanded in vitro then transplanted into immunocompromised mice to assess their developmental potentials in vivo. The progeny of cultured BMSSCs and DPSCs displayed distinct capacities, capable of regenerating the bone marrow and dental/pulp microenvironments, respectively (FIG. 5E, F), and appeared identical to the developmental potential of non-selected multi-colony derived BMSSCs and DPSCs (4).

Discussion

The present study provides direct evidence that two mesenchymal stem cell populations, distinct in their ontogeny and developmental potentials, are both associated with the microvasculature of their respective tissues.

We employed different immunoselection protocols to demonstrate that BMSSCs and DPSCs could be efficiently retrieved from bone marrow aspirates and enzyme digested pulp tissue respectively, based primarily on their high expression of the STRO-1 antigen. This cell surface antigen is present on precursors of various stromal cell types including, marrow fibroblasts, osteoblasts, chondrocytes, adipocytes, and smooth muscle cells isolated from human adult and fetal bone marrow.[29,32-34] Previous studies have implicated STRO-1 as a marker of pre-osteogenic populations, where its expression is progressively lost following cell proliferation and differentiation into mature osteoblasts in vitro.[27,35,36] The STRO-1 antigen was also found to be present on the outer cell walls of human bone marrow and dental pulp blood vessels, in accord with previous studies that localized STRO-1 on large blood vessels, but not capillaries, in different adult tissues such as brain, gut, heart, kidney, liver, lung, lymphnode, muscle, thymus.[6] Therefore, STRO-1 appears to be an early marker of different mesenchymal stem cell populations and infers a possible perivascular niche for these stem cell populations in situ.

To determine if BMSSCs and DPSCs were associated directly with blood vessels we utilized another antibody (CC9),[28] which recognizes the immunoglobulin super family member, CD146 (MUC-18/Mel-CAM), known to be present on smooth muscle, endothelium, myofibroblasts and Schwann cells in situ, as well as being a marker for some human neoplasms.[37] Notably, CD146 is not expressed by bone marrow hematopoietic stem cells, nor their progenitors. While the precise function of CD146 is not known, it has been linked to various cellular processes including cell adhesion, cytoskeletal reorganization, cell shape, migration and proliferation through transmembrane signaling.

In order to dissect the BMSSC population, STRO-1$^{BRT}$ expressing marrow cells were further distinguished from STRO-1$^+$ hematopoietic cells (predominantly glycophorin-A$^+$ nucleated erthrocytes) based on their expression of CD146, using dual-FACS analysis. Purified STRO-1$^{BRT}$/CD146$^+$ human BMSSCs displayed light scatter properties characteristic of large granular cells. Our study supports the findings of Van Vlasselaer and colleagues (1994)[38] who isolated partially purified BMSSCs from murine bone marrow following 5-fluoracil (5-FU) treatment, and identified this population as having high perpendicular and forward light scatter characteristics. Interestingly, freshly isolated 5-FU resistant murine BMSSCs were also found to be positive for two perivascular markers Sab-1 and Sab-2.[38] Conversely, more recent studies have shown that when BMSSCs are cultivated in vitro, the most primitive populations display low perpendicular and forward light scatter properties[39] and therefore may not reflect the true morphology of BMSSC in situ. In the present study, STRO-1$^{BRT}$/CD146$^+$ sorted human BMSSCs lacked the expression of CBFA1 and osteocalcin that identify committed early and late osteogenic populations, respectively,[40,41] indicating that BMSSCs exhibit a pre-osteogenic phenotype in human bone marrow aspirates. We found that a high proportion of freshly isolated STRO-1$^{BRT}$/CD146$^+$ BMSSCs expressed α-smooth muscle actin, but not the endothelial specific marker von Willebrand Factor, providing direct evidence that this primitive precursor population displays a characteristic perivascular phenotype.

The present study also demonstrated the efficacy of using magnetic bead selection to isolate and enrich for DPSCs directly from human dental pulp tissue based on their expression of either STRO-1 or CD146. Immunolocalization of CD146 appeared to be specific to the microvasculature within dental pup. Co-localization of both STRO-1 and CD146 on the outer walls of large blood vessel in dental pulp tissue, implied that the majority of DPSCs arise from the microvasculature. However, since the STRO-1 antibody also reacted with the perineurium in dental pulp and peripheral nerve bundles (unpublished observations), further investigation is required to determine the role of this antigen in neural cell development.

Analogous to BMSSCs, freshly isolated CD146+ DPSCs were found to express α-smooth muscle actin but not von Willebrand Factor. DPSCs were also shown to be an immature pre-odontogenic population both by their location distal from the dentin forming surface and by their lack of expression of the human odontoblast-specific dentin sialoprotein (DSP), which is restricted to the outer pulpal layer containing differentiated odontoblasts. We have previously described that ex vivo expanded human DPSCs do not express the precursor molecule, dentinsialophosphoprotein (DSPP), in vitro when cultured under non-inductive conditions.[4] Similar studies have shown that DSPP mRNA was highly expressed in freshly isolated odontoblast/pulp tissue, but was not detect in cultured dental papilla cells derived from rat incisors.[43,44] It is only when DPSCs are induced, either in vitro,[45] or by in vivo transplantation to form an ordered dentin matrix that DSPP is expressed.[4]

In vitro studies of ex vivo expanded BMSSCs and DPSCs supported the notion that their progeny were morphologically similar to cultured perivascular cells having a bi-polar fibroblastic, stellar or flat morphology, rather than a polygonal endothelial-like appearance. In addition, we have previously shown that the progeny of BMSSC- and DPSC-derived colonies exhibit heterogeneous staining for both CD146 and α-smooth muscle actin, but lack expression of the endothelial markers, CD34 and von Willebrand Factor, in vitro.[4]

The observations that two different mesenchymal stem cell populations such as BMSSCs and DPSCs harbour in perivascular niches may have further implications for identifying stem cell populations in other adult tissues. Recent findings have identified human "reserve" multi-potent mesenchymal stem cells in connective tissues of skeletal muscle, and dermis derived from human fetal and adult samples.[56] However the exact location, developmental potential and ontogeny of these stem cells is still largely unknown. In the present study, identification of mesenchymal stem cell niches in bone marrow and dentin pulp may help elucidate the fundamental conditions necessary to selectively maintain and expand primitive multi-potential populations in vitro, in order to direct their developmental potentials in vivo.

EXAMPLE 2

Adult Human Bone Marrow MPC are Distinct from Stromal Precursor Cells, Haematopoietic Stem Cells and Angioblasts by their High Expression of the STRO-1 Antigen and Lack of CD34 Expression Postnatal bone marrow appears to be a hub of residential stem and precursor cell types responsible for blood cell formation (haematopoietic stem cells), endothelial development (angioblast), and connective tissue/stromal differentiation (stromal precursor cells/bone marrow stromal stem cells/mesenchymal stem cells). Recent work by our group (Gronthos et al. 2003; Shi and Gronthos 2003) has, for the first time, purified and characterised human multipotential bone marrow mesenchymal precursor cells (MPC) based on their high expression of the STRO-1 antigen and by their co-expression of the immunoglobulin superfamily members, VCAM-1 (CD106) and MUC-18 (CD146). Early studies by Simmons and Torok-Storb (1991a and b), have shown that bone marrow-derived STRO-1+ stromal precursor cells, with the capacity to form adherent colonies in vitro, also expressed the haematopoietic stem cell marker, CD34, albeit at low levels. These studies used CD34 antibody-complement mediated cell lysis to eliminate a high proportion of adherent colony-forming cells in marrow aspirates (Simmons and Torok-Storb 1991b). It is important to note that while the STRO-1 antibody was generated following immunisation of mice with human CD34+ bone marrow cells, this may have arisen due to the fact that the STRO-1 antigen is also expressed at moderate to low levels on CD34+/Glycophorin-A+ nucleated red cells and CD34+/CD20+ B-lymphocytes. We now offer direct evidence, using sophisticated fluorescence activated cell sorting technology that multipotential adult human bone marrow MPC express high levels of STRO-1, but lack expression to the stromal precursor cell, haematopoietic stem cell and angioblast maker (CD34), the leukocyte antigen (CD45), and the nucleated red cell marker (Glycophorin-A) (FIG. 6A-C). These data demonstrate that adult human bone marrow-derived MPC are a novel stem cell population, distinct from more mature stromal precursor cells, haematopoietic stem cells and angioblast (FIG. 7).

Unless otherwise indicated the materials and methods of this example are the same as those for Example 1.

Figure 6:
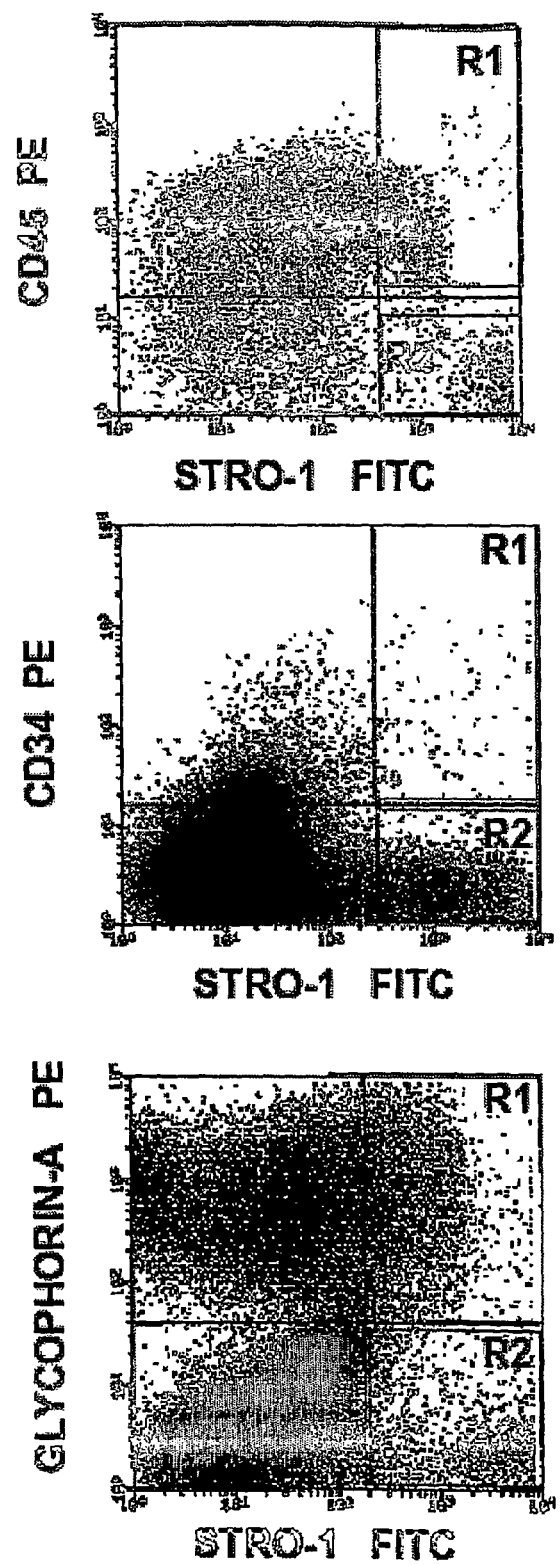
FIG. 6 Expression of CD34, CD45 and Glycophorin-A on STRO-1 positive bone marrow mononuclear cells. Representative histograms depicting typical dual-colour flow cytometric analysis profiles of STRO-1 positive bone marrow mononuclear cells isolated initially by magnetic activated sorting and co-stained with antibodies directed against CD34 (A), CD45 (B) or Glycophorin-A (C). The STRO-1 antibody was identified using a goat anti-murine IgM-fluorescein isothiocyanate while CD34, CD45 and Glycophorin-A were identified using a goat anti-murine IgG-phycoerythrin. The high expressing STRO-1 fraction which contained the clonogenic MPC population was isolated by fluorescence activated cell sorting based on regions R1 and R2.

FIG. 6. Expression of CD34, CD45 and Glycophorin-A on STRO-1 positive bone marrow mononuclear cells. Representative histograms depicting typical dual-colour flow cytometric analysis profiles of STRO-1 positive bone marrow mononuclear cells isolated initially by magnetic activated sorting and co-stained with antibodies directed against CD34 (A), CD45 (B) or Glycophorin-A (C). The STRO-1 antibody was identified using a goat anti-murine IgM-fluorescein isothiocyanate while CD34, CD45 and Glycophorin-A were identified using a goat anti-murine IgG-phycoerythrin. The high expressing STRO-1 fraction which contained the clonogenic MPC population was isolated by fluorescence activated cell sorting based on regions R1 and R2.

Figure 7:
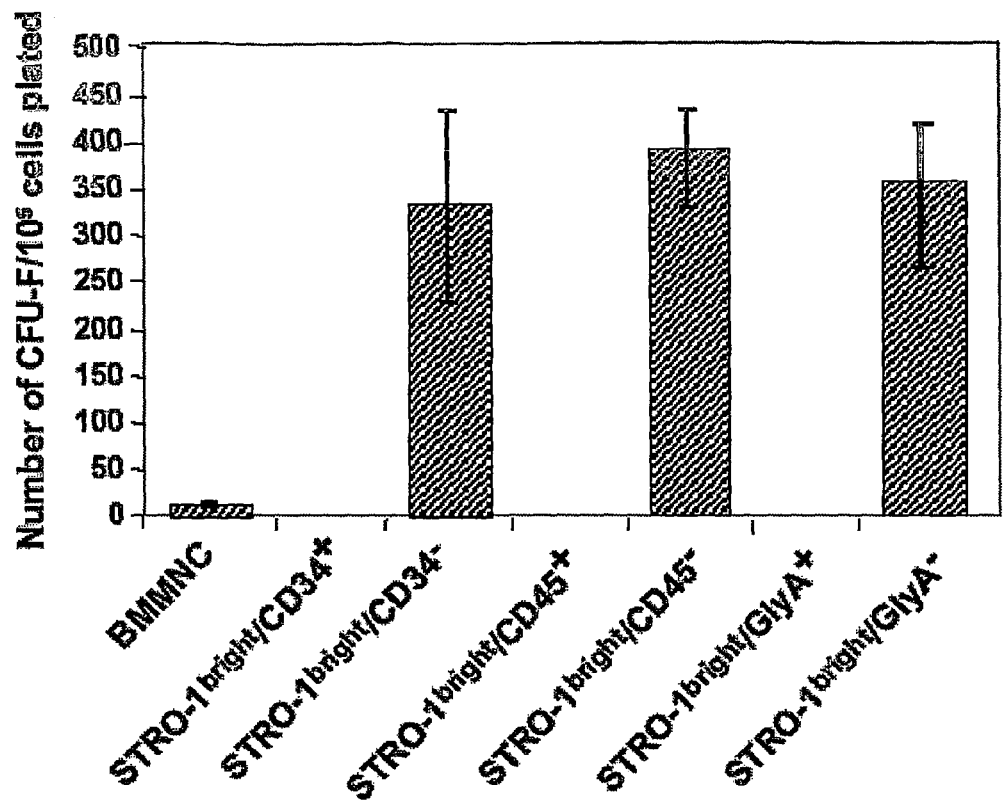
FIG. 7 Bone marrow MPC are STRO-1 bright, CD34 negative, CD45 negative and Glycophorin-A negative. The graph depicts the results of in vitro adherent colony formation assays performed for each of the different sorted STRO-1 bright populations selected by their co-expression or lack of either the CD34, CD45 or Glycophorin-A antigens, based on regions R1 and R2 as indicated in FIG. 6. These data are expressed as the mean incidence of colony-forming units for each cell fraction averaged from two separate experiments.
Figure 8A:
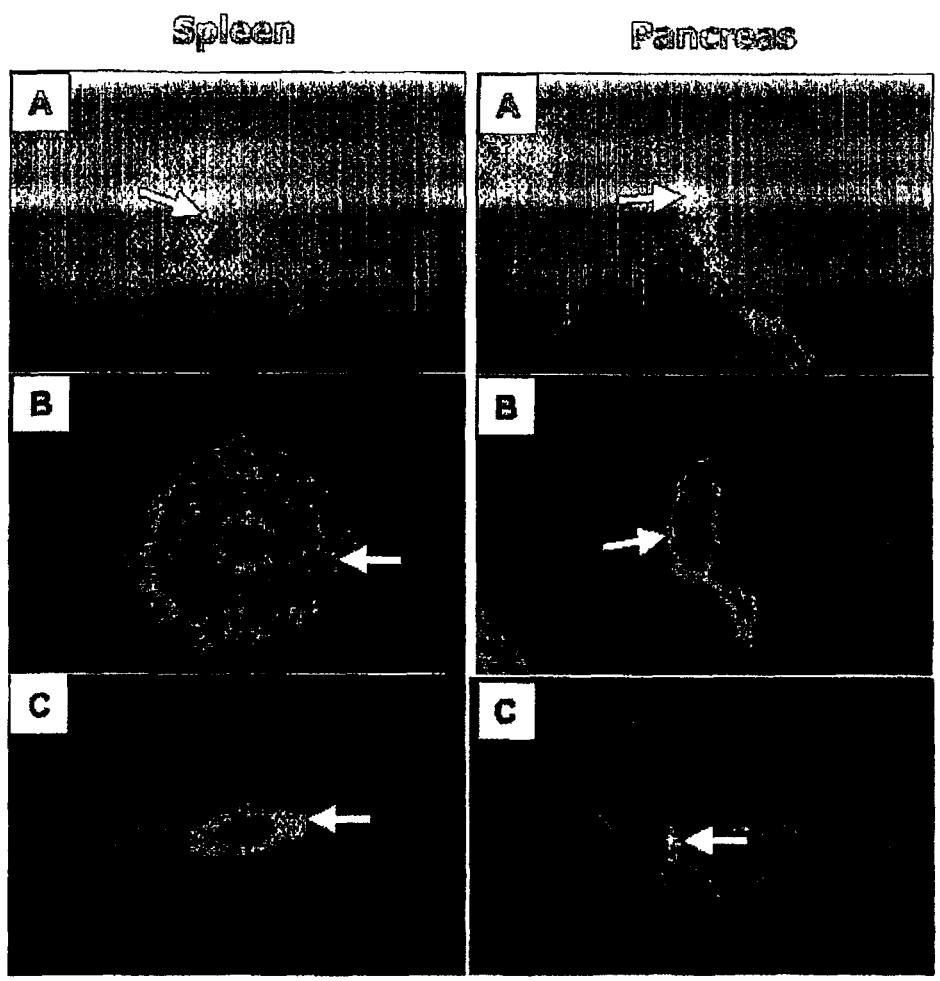
FIG. 8A-8D Reactivity of perivascular makers in different human tissues. Dual-colour immunofluorescence staining demonstrating reactivity of (A) STRO-1 and CD146, (B) STRO-1 and alpha-smooth muscle actin, and (C) 3G5 and CD146, on blood vessels and connective tissue present on spleen, pancreas (Panel 1), brain, kidney (Panel 2), liver, heart (Panel 3) and skin (Panel 4) 20.times. The STRO-1 and 305 antibodies were identified using a goat anti-murine IgM-Texas Red while CD146 and alpha-smooth muscle actin were identified using a goat anti-murine or IgG-fluorescein isothiocyanate. Co-localization is indicated by overlapping areas of yellow and orange fluorescence (white arrows).
Figure 8B:
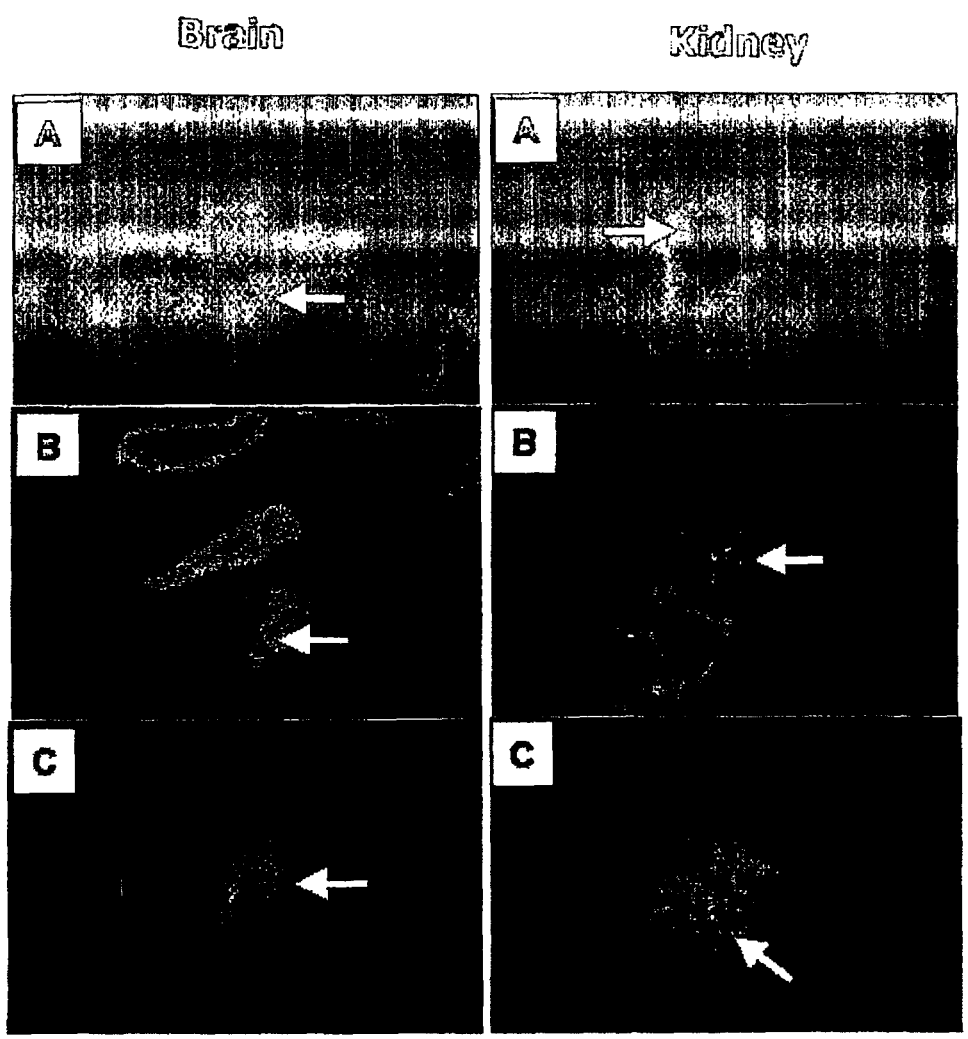
Figure 8C:
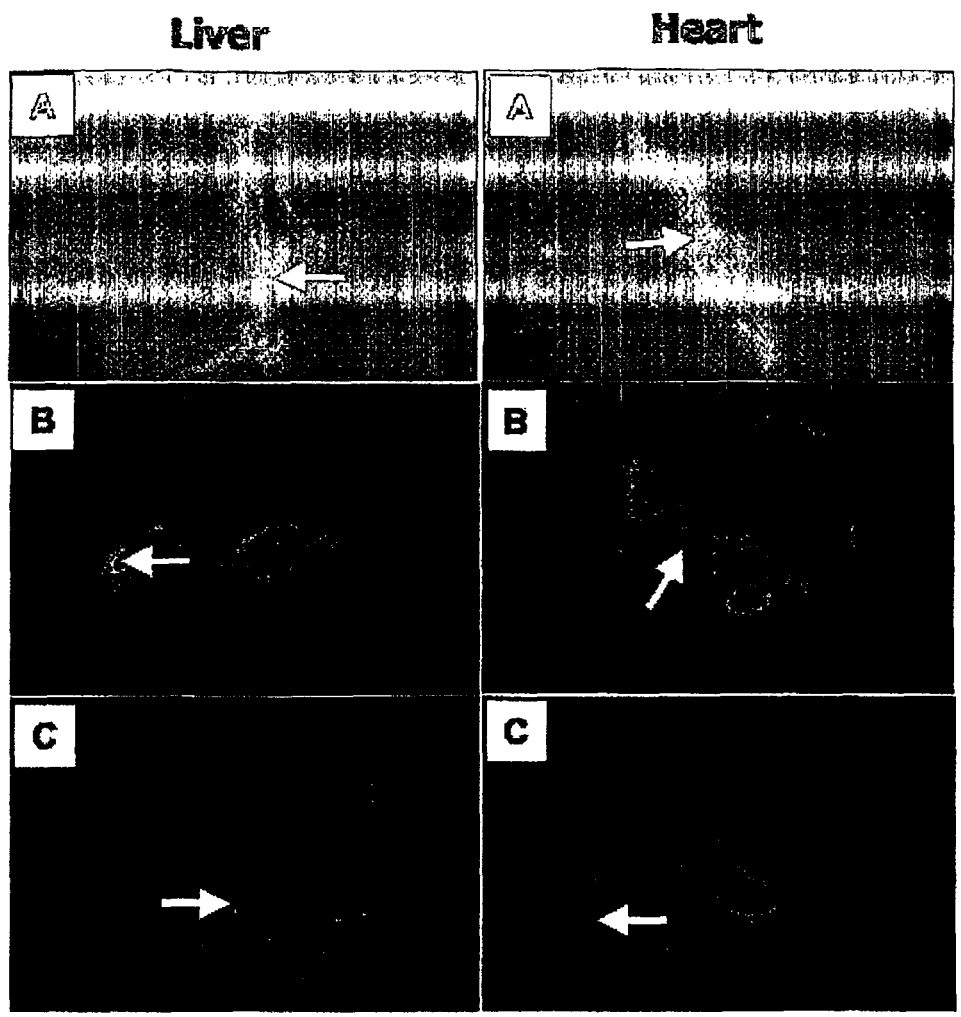
Figure 8D:
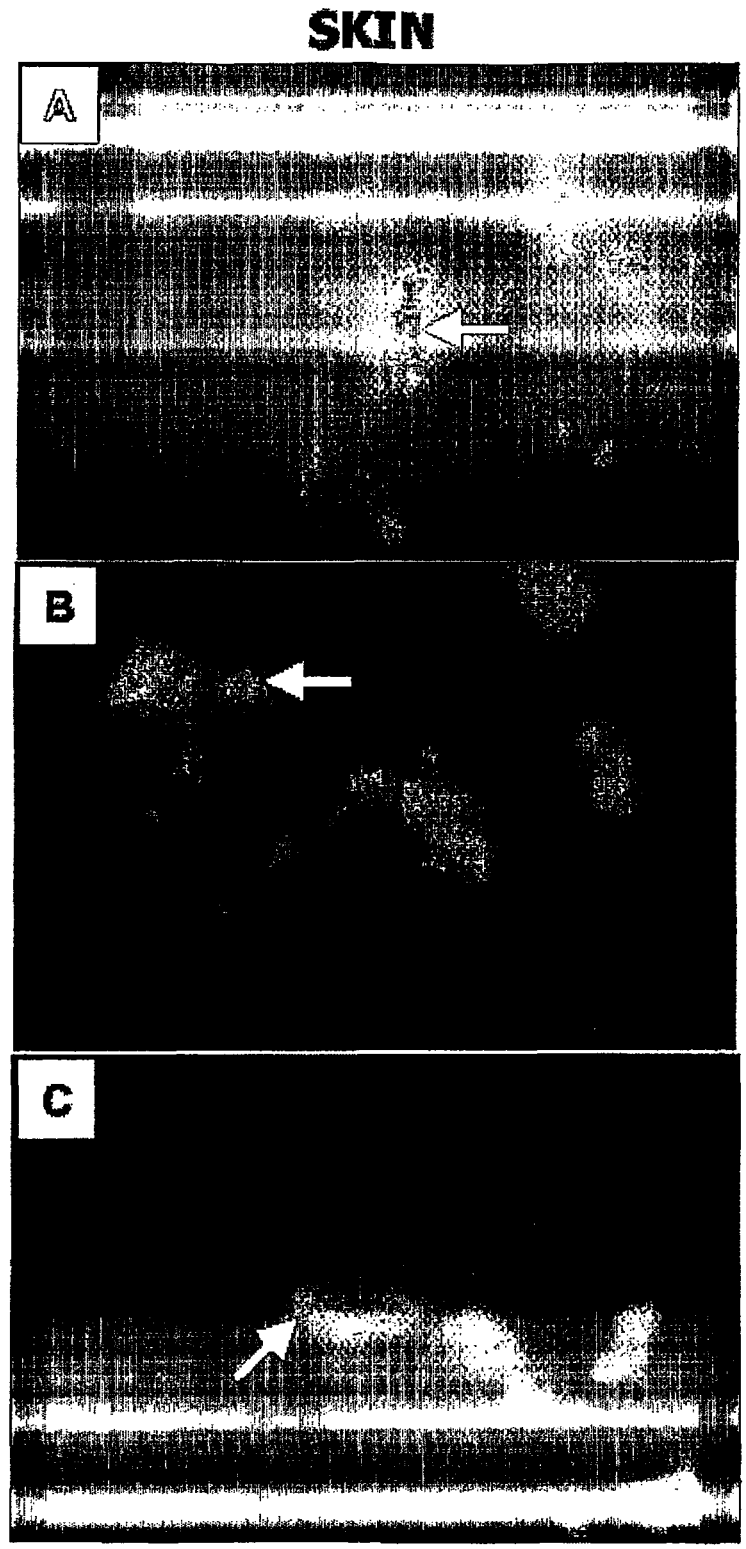

FIG. 7. Bone marrow MPC are STRO-1 bright, CD34 negative, CD45 negative and Glycophorin-A negative. The graph depicts the results of in vitro adherent colony formation assays performed for each of the different sorted STRO-1 bright populations selected by their co-expression or lack of either the CD34, CD45 or Gycophorin-A antigens, based on regions R1 and R2 as indicated in FIG. 6. These data are expressed as the mean incidence of colony-forming units for each cell fraction averaged from two separate experiments.

EXAMPLE 3

Identification of Multipotential MPC in Different Human Tissues

While the existence and precise location of MPC in different tissues is largely unknown, we have recently demonstrated that MPC appear to reside in a perivascular niche in human bone marrow and dental pulp tissues (Shi and Gronthos 2003). These observations were based on a combination of immunohistochemical and immunoselection methods to identify and isolate different MPC populations based on their expression of the mesenchymal stem cell marker, STRO-1, the smooth muscle and pericyte markers, CD146, alpha-smooth muscle actin and the pericyte specific marker, 3G5. We have now extended these studies demonstrating the co-localization of STRO-1/CD146, STRO-1/alpha-smooth muscle actin, and 3G5/CD146 antigens in a wider variety of tissues including heart, liver, kidney, skin, spleen, pancreas, lymph node (FIG. 8A-8D).

Figure 9:
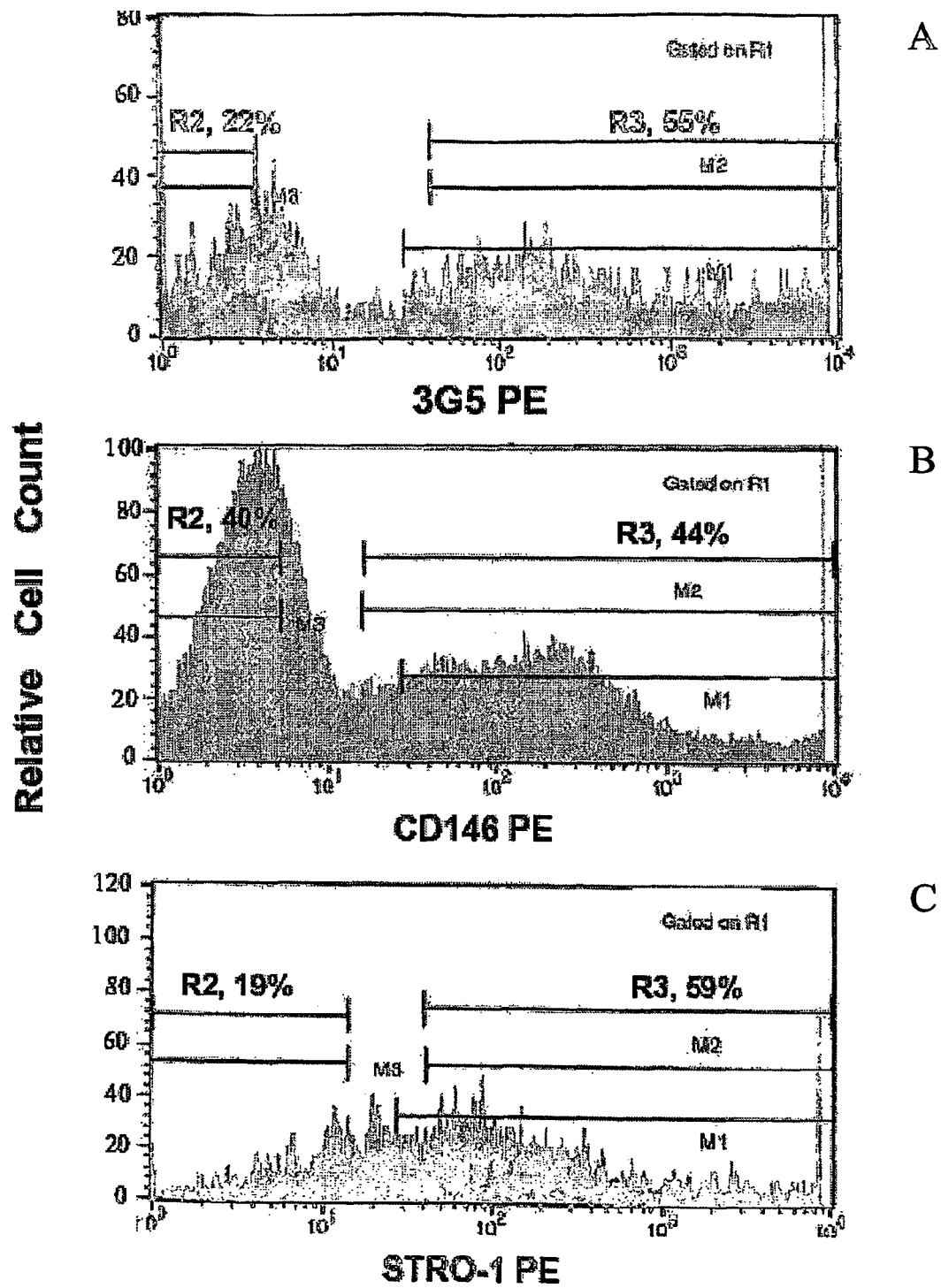
FIG. 9 Isolation of adipose-derived MPC by FACS. Representative flow cytometirc histograms depicting the expression of STRO-1, CD146 and 3G5 in fresh preparations of peripheral adipose-derived single-cell suspensions generated following collagenase/dispase digestion as previously described (Shi and Gronthos 2003). The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.
Figure 10:
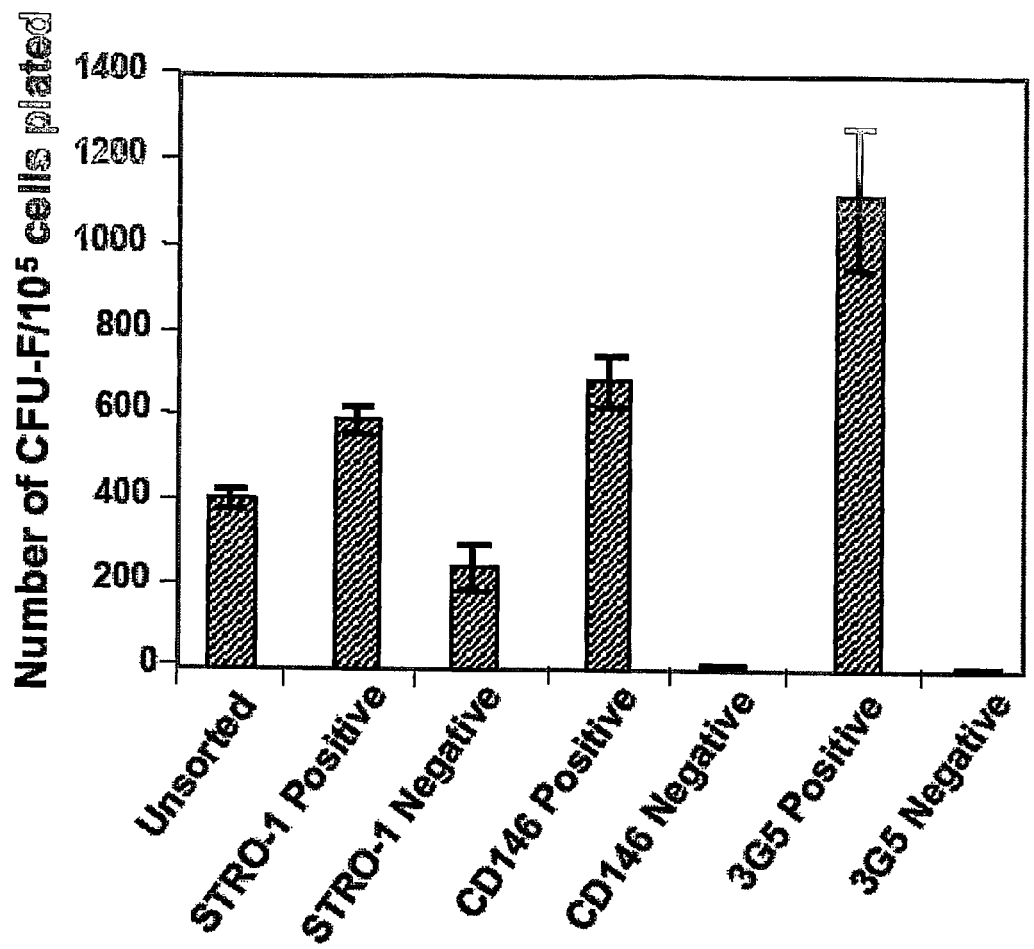
FIG. 10 Clonogenic adipose-derived MPC are positive for STRO-1/3G5/CD146. The bar graph depicts the number of clonogenic colonies retrieved from single cell suspensions of enzymatically digested human peripheral adipose tissue, following fluorescence activated cell sorting, based on their reactivity to antibodies that recognize STRO-1, CD146, and 3G5 (FIG. 9), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.
Figure 11:
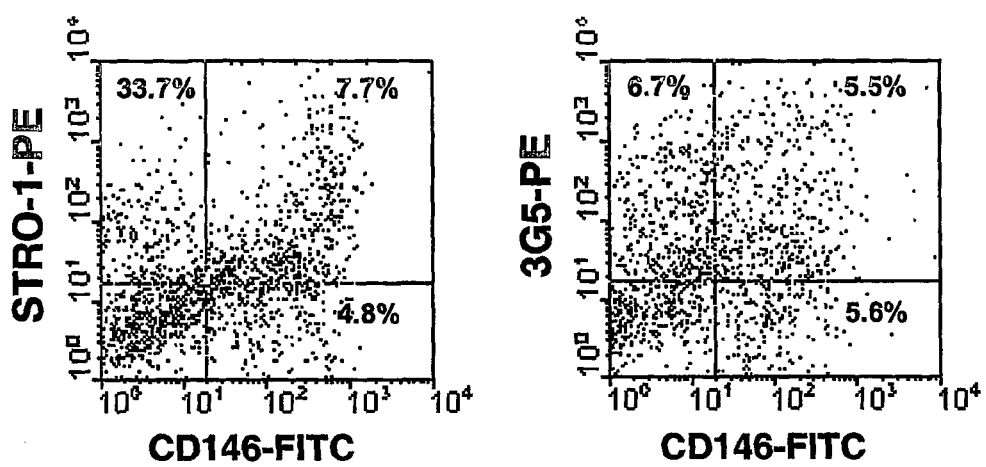
FIG. 11 Immunophenotypic analysis of adipose-derived MPC. Representative flow cytometric histograms depicting the co-expression of STRO-1 and CD146 (A) and 3G5 and CD146 in fresh preparations of peripheral adipose-derived single-cell suspensions generated following collagenase/dispase digestion. The STRO-1 and 3G5 antibodies were identified using a goat anti-murine IgM-phycoerythrin while CD146 was identified using a goat anti-murine IgG-fluorescein isothiocyanate.

To confirm our earlier findings that MPC can be derived from non-bone marrow tissue such as dental pulp, we used fluorescence activated cell sorting to isolate different MPC populations from adult human peripheral adipose. Single cell suspensions were obtained following digestion of the adipose tissue with collagenase and dispase as previously described (Shi and Gronthos 2003). The adipose-derived cells were then incubated with antibodies reactive against STRO-1, CD146 and 3G5. Cell populations were then selected by FACS, based on their positivity (region R3) or negativity (region R2) to each marker and then plated into regular growth medium (Shi and Gronthos 2003) to assess the incidence of adherent colony-forming cells in each cell fraction (FIG. 9). Following 12 days of culture, colonies (aggregates of 50 cells or more) were scored and displayed as the number of colonies per $10^5$ cells plated for each cell fraction. Our data demonstrated that MPC can be derived from adipose tissues based on their expression of STRO-1/3G5/CD146 antigens (FIG. 10). Dual colour flow cytometric analysis confirmed that only a minor proportion of adipose-derived cells co-expressed STRO-1/CD146 and 3G5/CD146 (FIG. 11). These findings are consistent with our previous observations that MPC can be isolated from both bone marrow and dental pulp tissue based on the same set of perivascular markers (Shi and Gronthos 2003). Furthermore, we provide evidence demonstrating that adipose derived MPC isolated by CD146 selection have the capacity to differentiate into different tissues such as bone, fat and cartilage (FIG. 12), as previous described (Gronthos et al. 2003).

Figure 13:
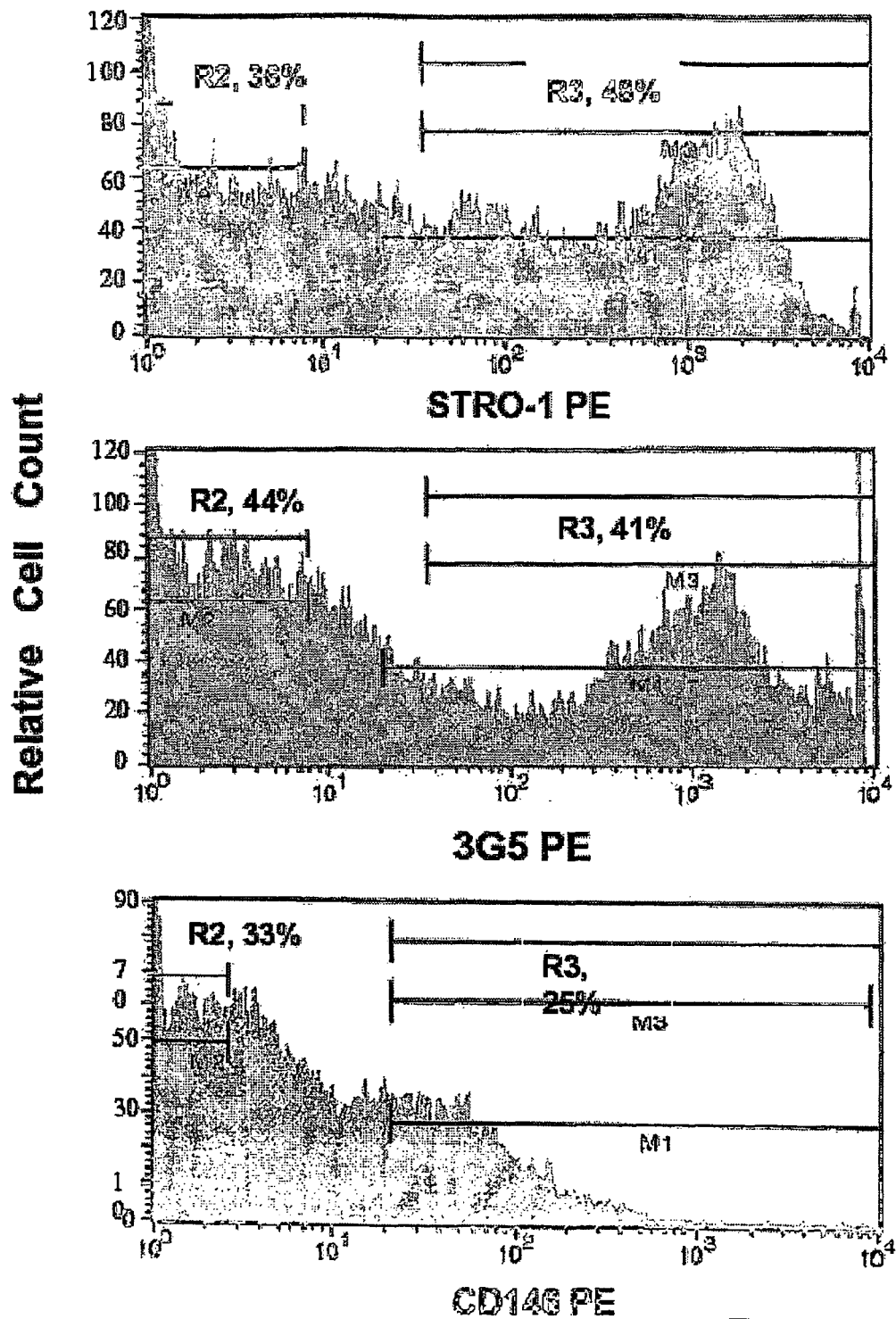
FIG. 13 Isolation of skin-derived MPC by FACS. Representative flow cytometirc histograms depicting the expression of STRO-1, CD146 and 3G5 in fresh preparations of full thickness skin-derived single-cell suspensions generated following collagenase/dispase digestion. The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

Recent findings examining the existence of MPC in unrelated tissues such as skin has also been examined to further strengthen our hypothesis. Single cell suspensions were obtained following digestion of full thickness human skin with collagenase and dispase as described above for human adipose tissue. The skin-derived cells were then incubated with antibodies reactive against STRO-1, CD146 and 3G5 identified using either a goat anti-murine IgM or IgG-phycoerythrin. Cell populations were then selected by FACS, based on their positivity (region R3) or negativity (region R2) to each marker and then plated into regular growth medium (Shi and Gronthos 2003) to assess the incidence of adherent colony-forming cells in each cell fraction (FIG. 13). Following 12 days of culture, colonies (aggregates of 50 cells or more) were scored and displayed as the number of colonies per $10^5$ cells plated for each cell fraction. The data demonstrated that MPC can also be derived from skin based on their expression of STRO-1/3G5/CD146 antigens (FIG. 10). Collectively these data suggest that multipotential MPC can be identified and isolated in virtually all vascularised tissues derived from postnatal human tissue based on a common phenotype.

Unless otherwise indicated the materials and methods of this example are the same as those for Example 1.

FIG. 8A-8D. Reactivity of perivascular makers in different human tissues. Dual-colour immunofluorescence staining demonstrating reactivity of (A) STRO-1 and CD146, (B) STRO-1 and alpha-smooth muscle actin, and (C) 3G5 and CD146, on blood vessels and connective tissue present on spleen, pancreas (Panel I), brain, kidney (Panel II), liver, heart (Panel III) and skin (Panel IV) 20.times. The STRO-1 and 3G5 antibodies were identified using a goat anti-murine IgM-Texas Red while CD146 and alpha-smooth muscle actin were identified using a goat anti-murine or IgG-fluorescein isothiocyanate. Co-localization is indicated by overlapping areas of yellow and orange fluorescence (white arrows).

FIG. 9. Isolation of adipose-derived MPC by FACS. Representative flow cytometric histograms depicting the expression of STRO-1, CD146 and 3G5 in fresh preparations of peripheral adipose-derived single-cell suspensions generated following collagenase/dispase digestion as previously described (Shi and Gronthos 2003). The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

FIG. 10. Clonogenic adipose-derived MPC are positive for STRO-1/3G5/CD146. The bar graph depicts the number of clonogenic colonies retrieved from single cell suspensions of enzymatically digested human peripheral adipose tissue, following fluorescence activated cell sorting, based on their reactivity to antibodies that recognize STRO-1, CD146, and 3G5 (FIG. 9), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

FIG. 11. Immunophenotypic analysis of adipose-derived MPC. Representative flow cytometric histograms depicting the co-expression of STRO-1 and CD146 (A) and 3G5 and CD146 in fresh preparations of peripheral adipose-derived single-cell suspensions generated following collagenase/dispase digestion. The STRO-1 and 3G5 antibodies were identified using a goat anti-murine IgM-phycoerythrin while CD146 was identified using a goat anti-murine IgG-fluorescein isothiocyanate. Approximately 60% and 50% of the CD146 positive cells co-express STRO-1 and 3G5, respectively. These data suggest that 10% or more of the CD164 positive cells co-express STRO-1 and 3G5.

Figure 12:
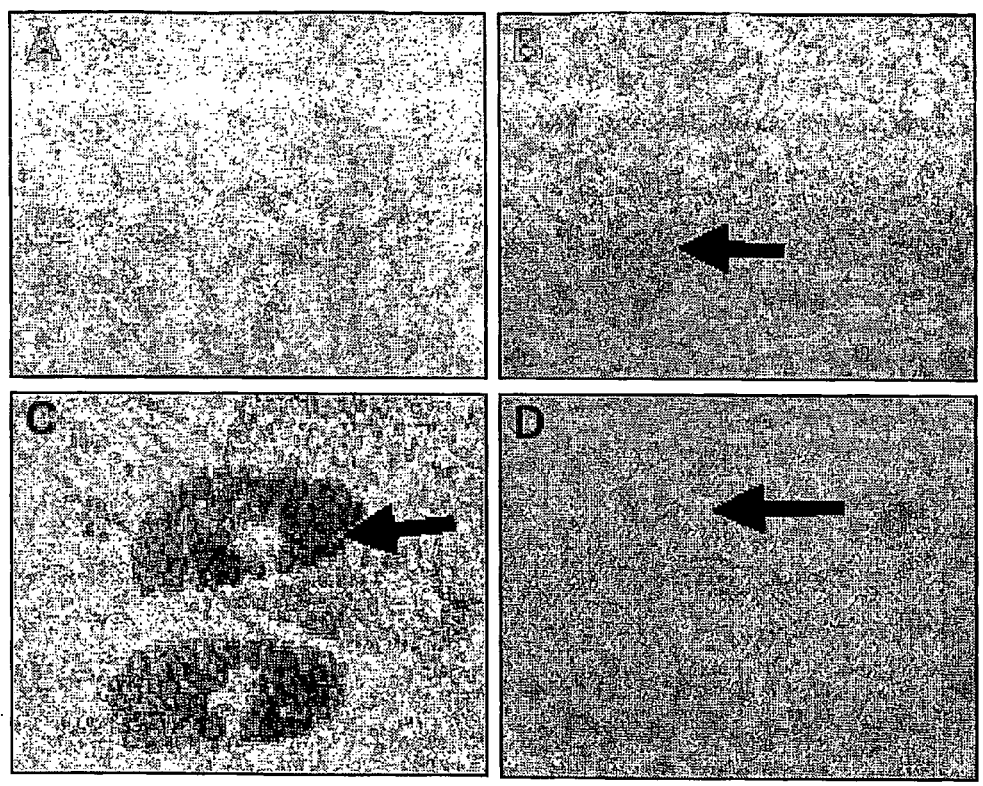
FIG. 12 Developmental potential of purified Adipocyte-derived MPC in vitro. Preparations of primary MPC cultures derived from STRO-1$^+$/CD146$^+$ adipose cells were re-cultured either in standard culture conditions (A), osteogenic inductive medium (B), Adipogenic inductive medium (C) or condrogenic conditions (D) as previously described Gronthos et al. 2003. Following two weeks of multi-differentiation induction, the adipocyte-derived MPC demonstrated the capacity to form bone (B; Alizarin positive mineral deposits), fat (C; Oil Red O positive lipid) and cartilage (D: collagen type II matrix).

FIG. 12. Developmental potential of purified Adipocyte-derived MPC in vitro. Preparations of primary MPC cultures derived from STRO-1$^+$/CD146$^+$ adipose cells were re-cultured either in standard culture conditions (A), osteogenic inductive medium (B), Adipogenic inductive medium (C) or condrogenic conditions (D) as previously described Gronthos et al. 2003. Following two weeks of multi-differentiation induction, the adipocyte-derived MPC demonstrated the capacity to form bone (B; Alizarin positive mineral deposits), fat (C; Oil Red O positive lipid) and cartilage (D: collagen type II matrix).

FIG. 13. Isolation of skin-derived MPC by FACS. Representative flow cytometirc histograms depicting the expression of STRO-1, CD146 and 3G5 in fresh preparations of full thickness skin-derived single-cell suspensions generated following collagenase/dispase digestion. The antibodies were identified using either a goat anti-murine IgM or IgG-phycoerythrin. Cell populations were then selected by FACS, based on their positivity (region R3) or negativity (region R2) to each marker and then plated into regular growth medium to assess the incidence of adherent colony-forming cells in each cell fraction.

Figure 14:
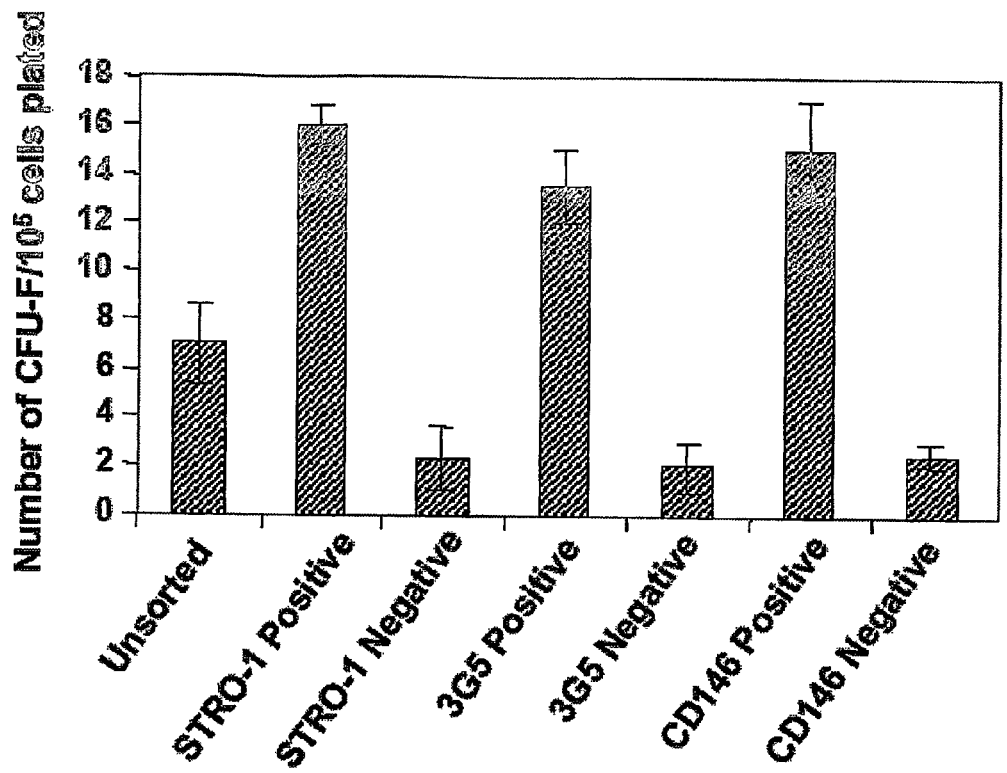
FIG. 14 Clonogenic skin-derived MPC are positive for STRO-1/3G5/CD146. The bar graph depicts the number of adherent colonies recovered from single cell suspensions of enzymatically digested human skin, following fluorescence activated cell sorting, based on their reactivity to antibodies that recognize STRO-1, CD146, and 3G5 (FIG. 6), then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

FIG. 14. Clonogenic skin-derived MPC are positive for STRO-1bri/3G5/CD146. The bar graph depicts the number of adherent colonies recovered from single cell suspensions of enzymatically digested human skin, following fluorescence activated cell sorting, based on their reactivity to antibodies that recognize STRO-1, CD146, and 3G5, then cultured in standard growth medium as previously described for bone marrow and dental pulp tissue (Shi and Gronthos 2003). The data are expressed as the number of colony-forming units obtained per $10^5$ cells plated in the positive and negative cell fractions averaged from two separate experiments.

EXAMPLE 4

Figure 15:
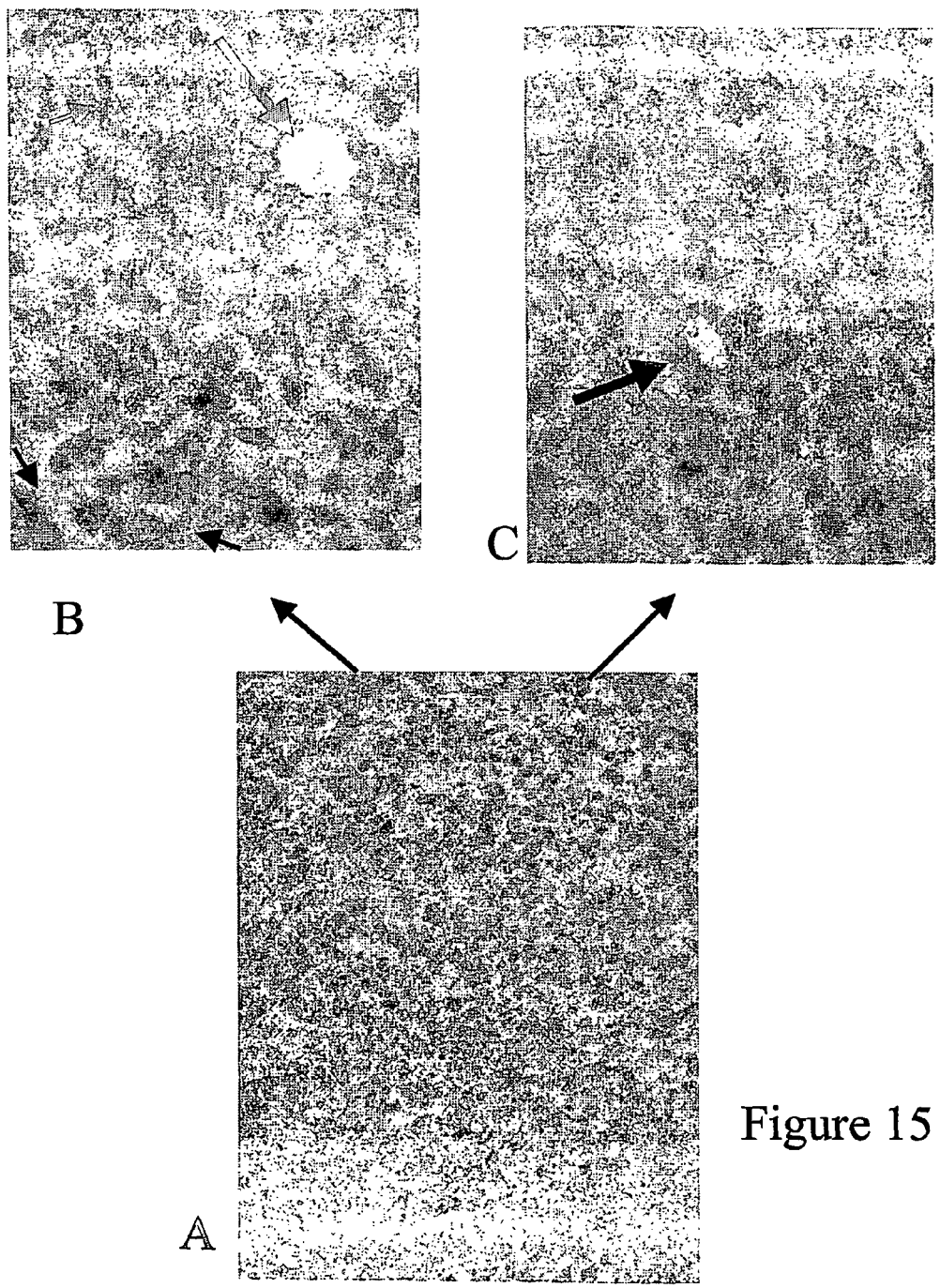
FIG. 15 Prominent in vivo survival of cultured STRO1$^{bright}$ cells adjacent to blood vessels.

Stro$^{bright}$ Cells Induce Neovasculanzation (Angiogenesis and Arteriogenesis) and Result in Functional Improvement of Ischemic Myocardial Tissue FIG. 15. Engraftment and Survival of Human Stro$^{bright}$ Cells Injected Into Rat Tumors. Athymic nude rats were irradiated with 250 Gy for 5 minutes to remove residual natural killer function, then injected subcutaneously in the flank with $1\times10^6$ rat glioblastoma cells. Two weeks after implantation, the glioblastoma tumors were directly injected with either 500,000 Stro$^{bright}$ cells, 500,000 Stro$^{dim}$ cells or saline, and animals were sacrificed 7 days later. In 2/3 tumor tissues which received Stro$^{bright}$ cells, staining by immunoperoxidase method using a monoclonal antibody with specific reactivity against human, but not rat, mitochondria, demonstrated numerous human cells around the injection site, indicating medium-term engraftment and survival. Human cells were not detected in any of the three tissues receiving Stro$^{dim}$ cells, suggesting that Stro$^{bright}$ cells might have a survival or replicative advantage in this in vivo model system (see panel A). The Stro$^{bright}$ cells were predominantly in clusters nearby small capillaries and arterioles (small arrows) (panel B). In addition, several human cells were seen to incorporate into vascular structures (large arrow) (panel C). These data indicate that human Stro$^{bright}$ cells can both induce neovascularization of endogenous (rat) vessels and can become incorporated into new vessels of human origin.

Figure 16:
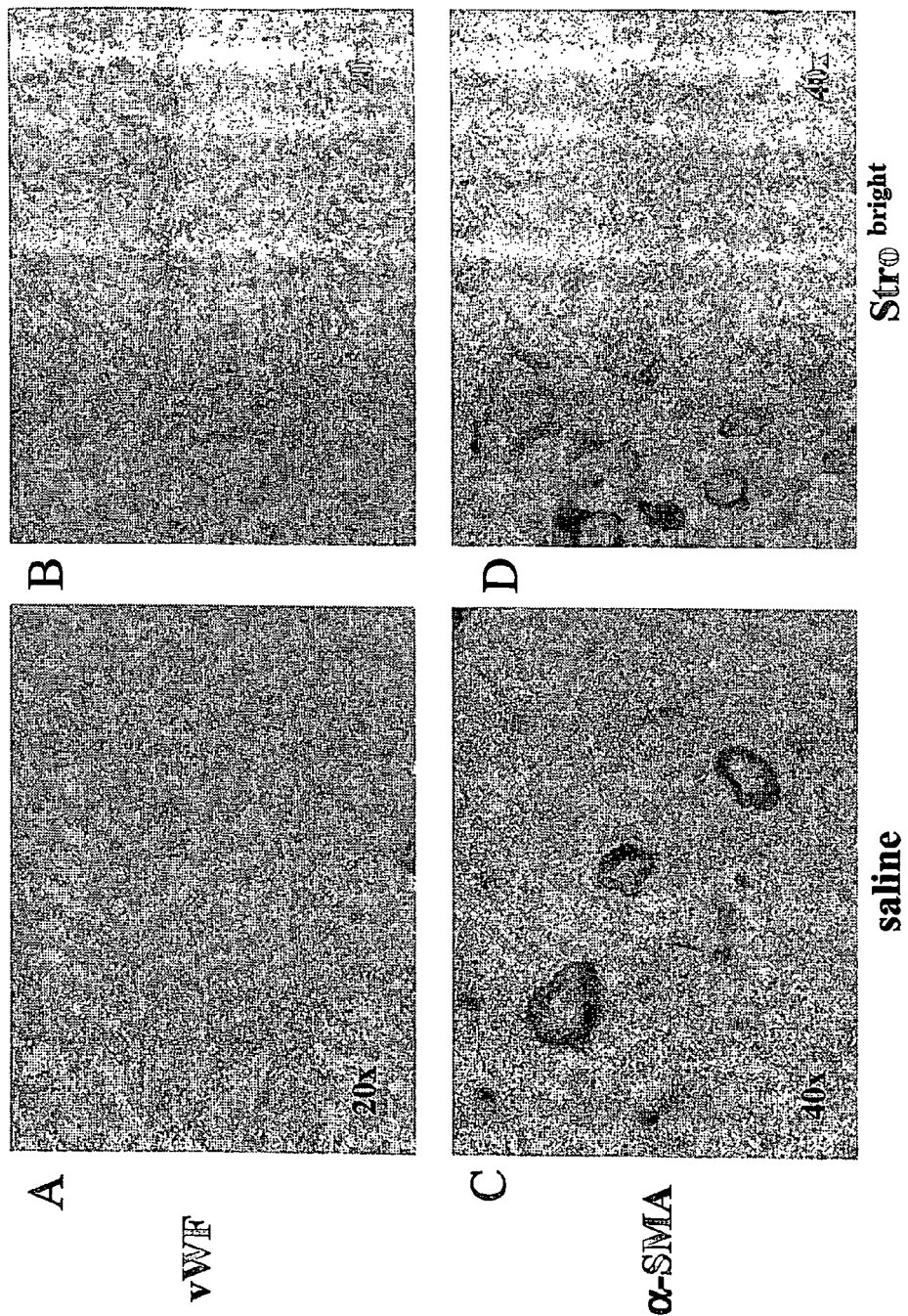
FIG. 16 Tumour arteriogenesis induced by cultured STRO1$^{bright}$ cells

FIG. 16. Induction Of Tumor Neovascularization (Angiogenesis And Arteriogenesis) By Human Stro$^{bright}$ Cells. In consecutive sections of the tumor tissue stained by immunoperoxidase method using monoclonal antibodies directed, respectively, against von Willebrand Factor (vWF) and alpha-smooth muscle actin (alpha-SMA), animals injected with Stro$^{bright}$ cells demonstrated significantly greater numbers of capillaries and arterioles (defined, respectively, by vWF staining alone and combined expression of vWF and alpha-SMA) than animals injected with saline.

Figure 17:
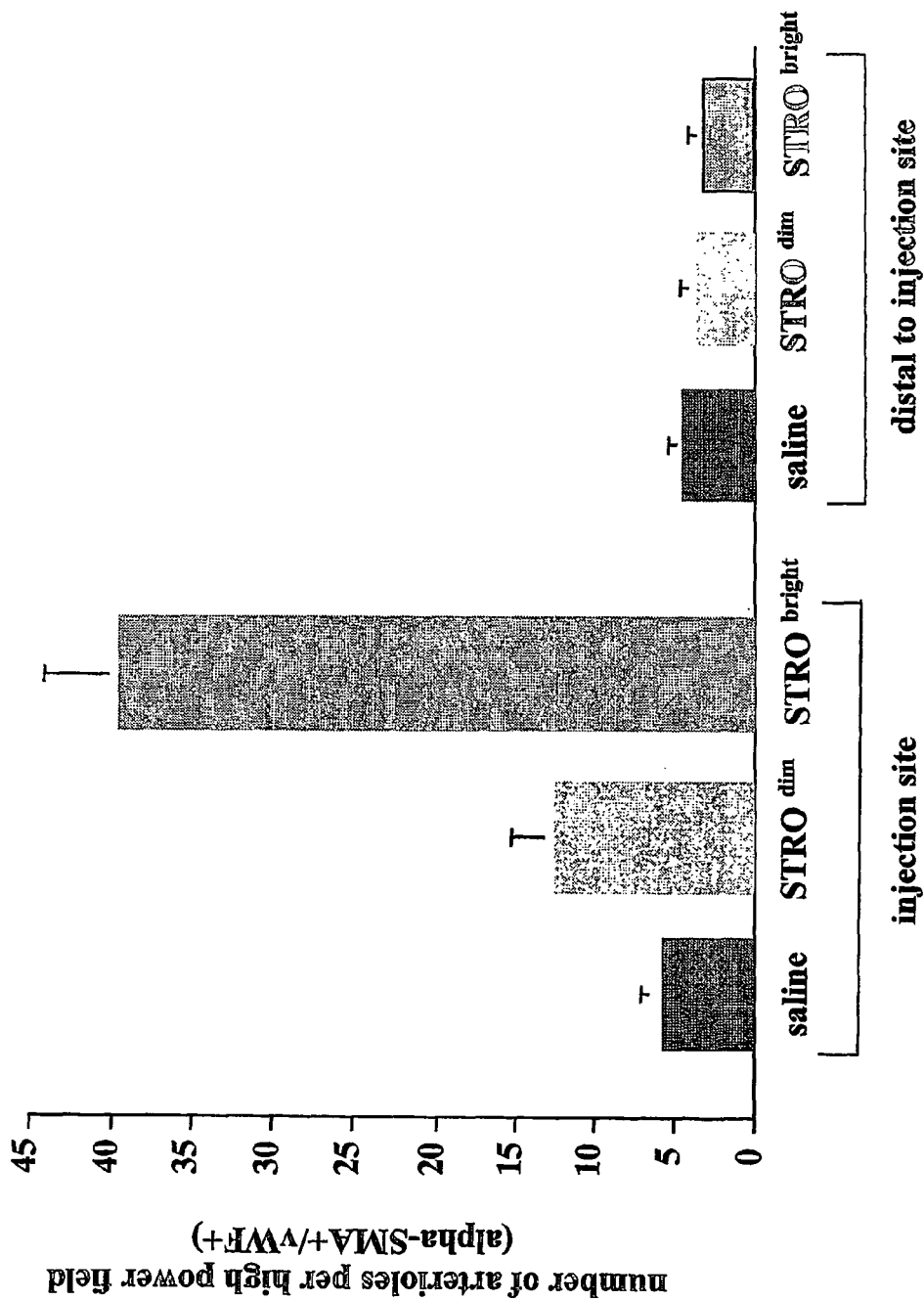
FIG. 17 Tumor arteriogenesis induced by progeny of STRO1$^{bright}$ cells

FIG. 17. Stro$^{bright}$ Cells Are More Potent Inducers Of Neovascularization (Angiogenesis And Arteriogenesis) Than Stro$^{dim}$ Cells. Quantitation of arteriolar numbers (defined as vascular structures with lumen diameter >50 microns and circumferential expression of alpha-SMA) demonstrated that animals injected with Stro$^{bright}$ cells had almost eight-fold greater number of arterioles than saline-treated controls at the site of injection (40±5 vs 6±2 arterioles/high power field, p<0.01), while no difference could be detected distal to the injection site. Animals injected with the Stro$^{dim}$ progeny demonstrated a modest, two-fold increase in the number of arterioles at the injection site relative to saline-treated controls (13±3 vs 6±2 arterioles/high power field, p<0.01), indicating that the Stro$^{bright}$ progeny contained the most potent pro-arteriogenic cells following in vitro culture.

Figure 18:
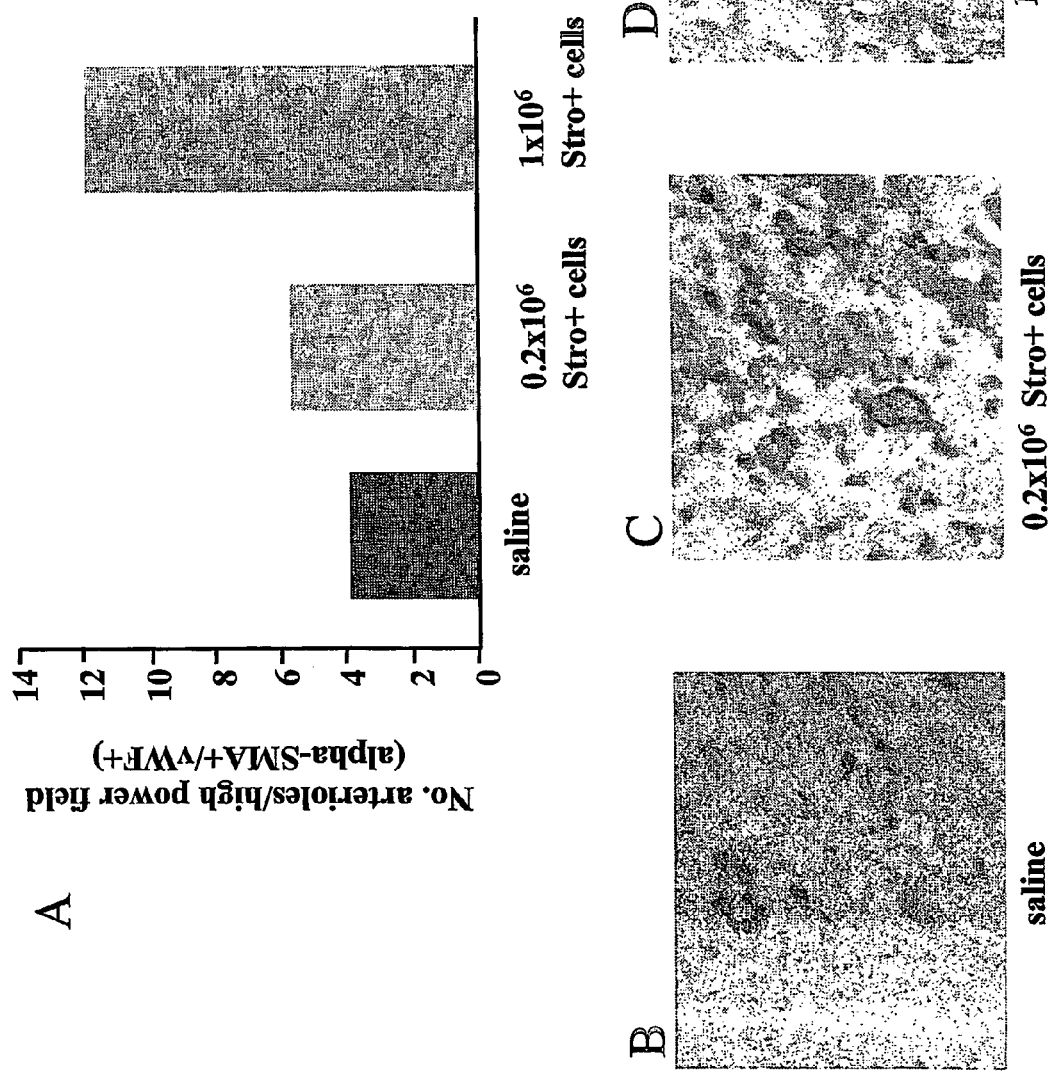
FIG. 18 Dose-dependent cardiac arteriogenesis by cultured STRO1$^{bright}$ cells.

FIG. 18. Dose-Dependent Effect Of Stro$^{bright}$ Cells On Myocardial Neovascularization. To examine whether induction of angiogenesis and arteriogenesis could be extended to other tissues, and was associated with biological significance, cultured progeny of Stro-selected cells were injected by direct intramyocardial injection into the peri-infarct regions of the ischemic hearts in athymic nude rats who had undergone left anterior descending coronary artery (LAD) ligation two days earlier. Animals injected with $1\times10^6$ Stro$^{bright}$ cells demonstrated three-fold greater numbers of arterioles at the peri-infarct region than animals injected with saline (12±2 vs 4±1 arterioles/high power field, p<0.01). In contrast, animals injected with only $0.2\times10^6$ Stro$^{bright}$ cells, delivered in a total of $1\times10^6$ unfractionated cultured progeny of Stro-selected cells, induced only 50% greater numbers of arterioles at the peri-infarct region than saline (6±1 vs 4±1 arterioles/high power field, p<0.05), indicating that Stro$^{bright}$ cells have a dose-dependent effect on arteriolar induction in the ischemic heart.

Figure 19:
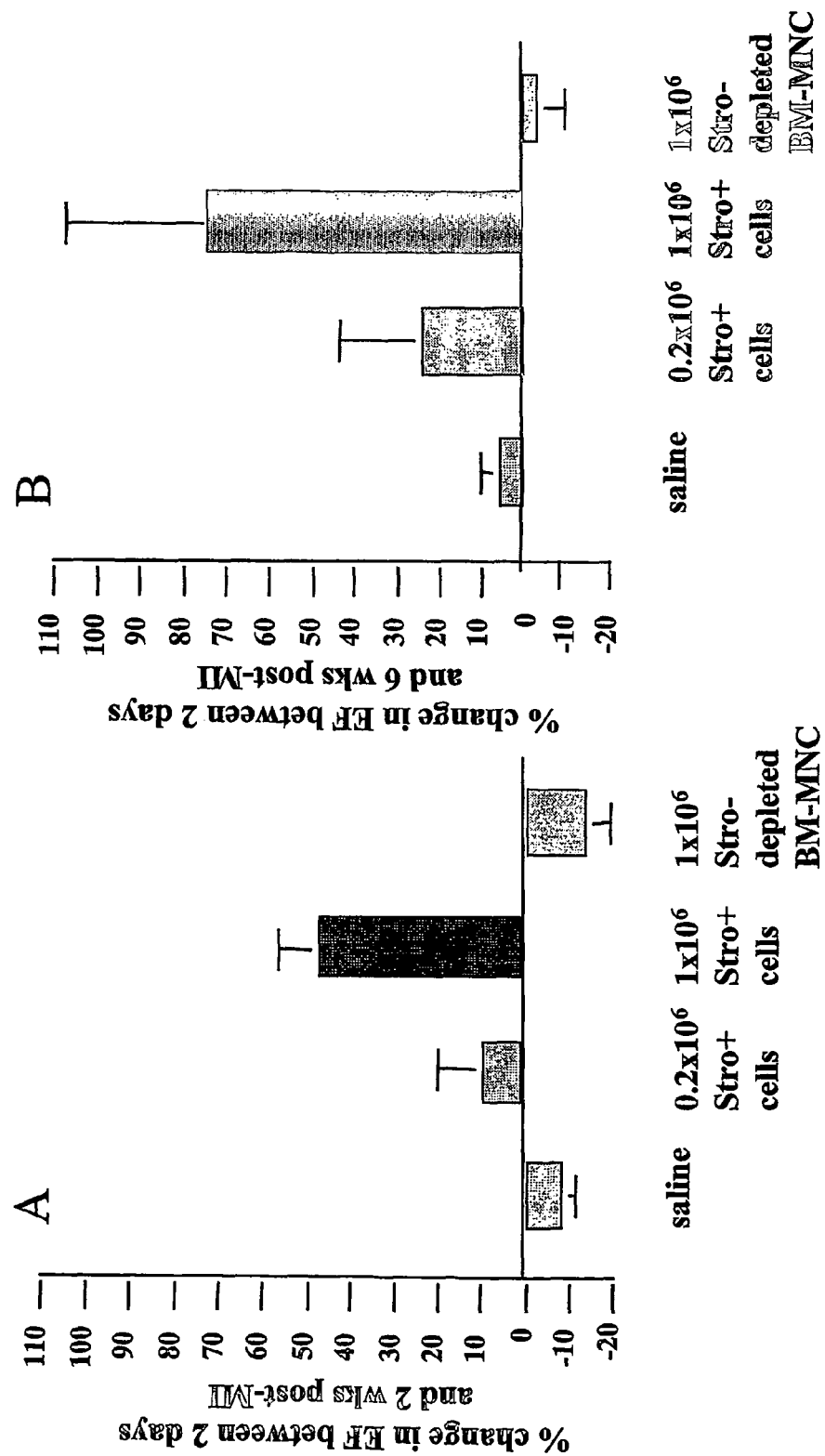
FIG. 19 Improvement in left ventricular ejection fraction (EF) by myobardial injection of cultured STRO1$^{bright}$ cells.
Figure 20:
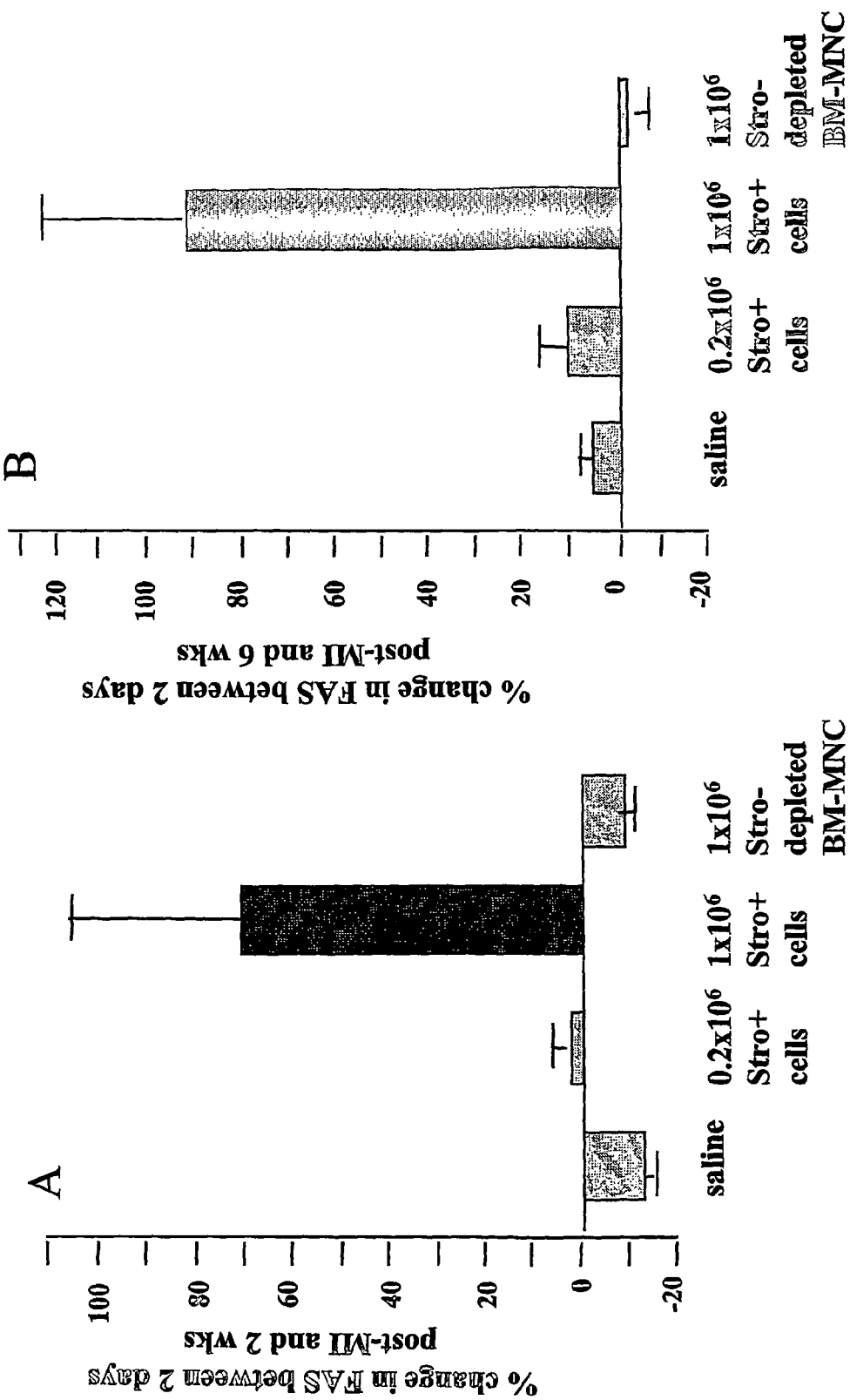
FIG. 20 Improvement in left ventricular fractional area shortening (FAS) by myocardial injection of cultured STRO1$^{bright}$ cells.
Figure 21:
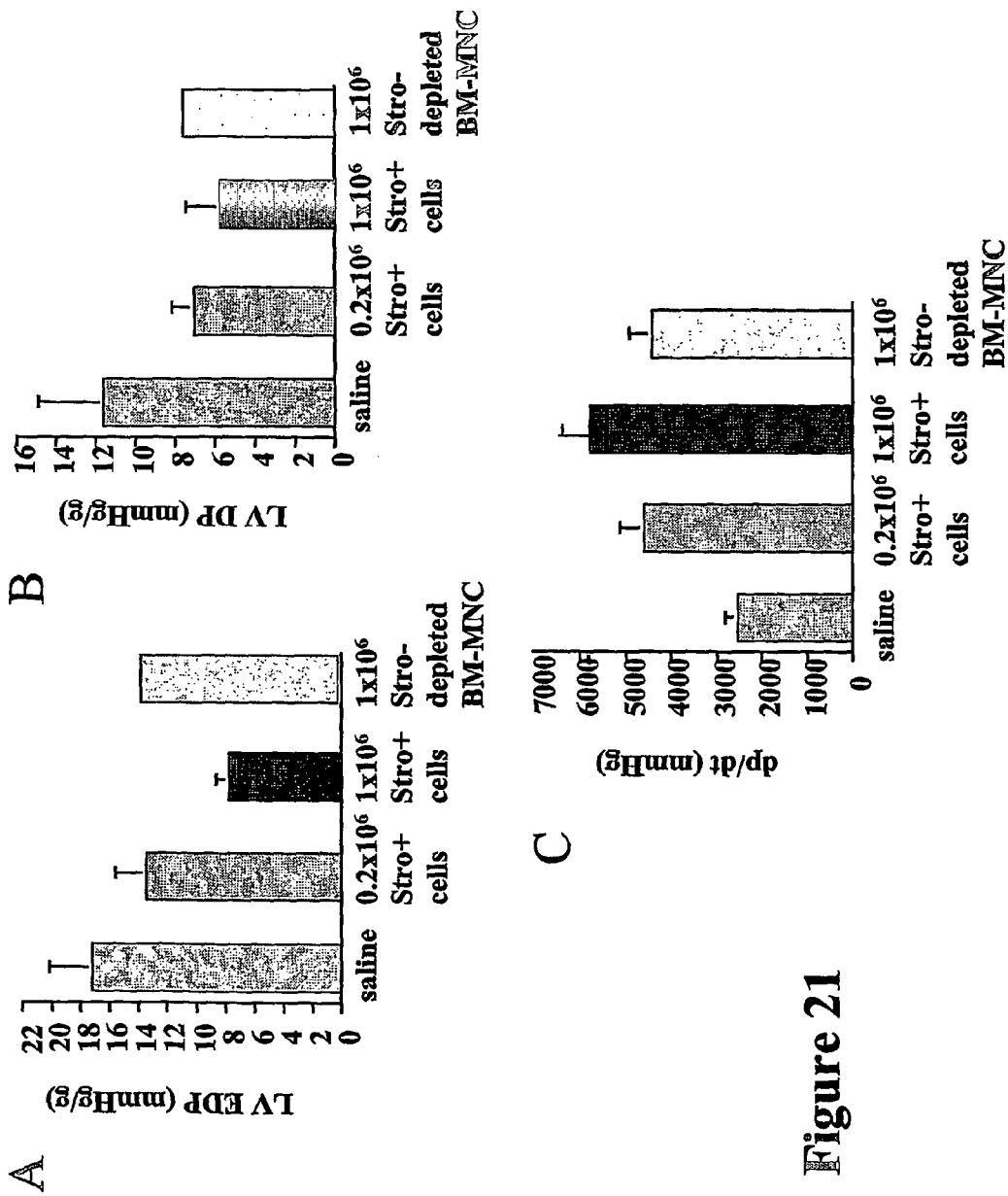
FIG. 21 Improvement in global cardiac function by myocardial injection of cultured STRO1$^{bright}$ cells.

FIGS. 19, 20 and 21. Stro$^{bright}$-Dependent Myocardial Neovascularization Results In Global Improvement of Parameters Of Myocardial Function. We next examined the effects of Stro$^{bright}$-dependent myocardial neovascularization on global parameters of cardiac function. As shown in FIG. 19, injection of about $0.1-0.2\times10^6$ and $1\times10^6$ Stro$^{bright}$ cells resulted in dose-dependent improvement in ejection fraction (EF) at 2 and 6 weeks, as measured by echocardiography performed and analyzed by a blinded technician. Animals receiving $1\times10^6$ Stro$^{bright}$ cells demonstrated mean improvement in EF at 2 and 6 weeks of 50% and 75%, respectively, relative to baseline values two days post-LAD ligation. In stark contrast, saline-treated animals showed only 5% mean improvement in EF by 6 weeks (p<0.01), and animals treated with Stro-depleted fresh bone marrow mononuclear cells demonstrated no difference compared with those receiving saline. Injection of $1\times10^6$ Stro$^{bright}$ cells resulted in similar dramatic improvement in fractional area shortening (FAS) (mean improvement of 70% and 90% at 2 and 6 weeks, respectively, FIG. 20). Stro-depleted bone marrow mononuclear cells again had no effect, while modest improvement was seen after injection of about $01.-0.2\times10^6$ Stro$^{bright}$ cells. Finally, as shown in FIG. 21, injection of $1\times10^6$ Stro$^{bright}$ cells resulted in significant improvement in left ventricular compliance compared with saline-treated controls. Animals receiving Stro$^{bright}$ cells demonstrated over 50% reduction in both left ventricular mean end-diastolic pressure and diastolic pressure (each p<0.01), and over two-fold improvement in dp/dt (p<0.01). Together, these results indicate that the neovascularization (angiogenesis and arteriogenesis) of ischemic rat myocardium induced by injection of $1\times10^6$ human Stro$^{bright}$ cells resulted in significant improvement in both global systolic and diastolic parameters of cardiac function.

EXAMPLE 5

Immunophenotypic Analysis of Ex Vivo Expanded Human Bone Marrow Mesenchymal Precursor Cells We have previously reported that multipotential mesenchymal precursor cells (MPC) can be purified from adult human bone marrow mononuclear cells based on the phenotype STRO-1$^{bright}$/VCAM-1 (CD106)$^+$ or STRO-1$^{bright}$/C-18 (CD146)$^+$ (Gronthos et al. 2003; Shi and Gronthos 2003). The MPC population can be readily propagated in vitro under defined culture conditions (Gronthos et al. 2003). We now present data characterising the ex vivo expanded MPC progeny based on markers associated with different cell lineages, at both the mRNA and protein level, using reverse transcriptase-polymerase chain reaction (RT-PCR) and flow cytometric analysis, respectively.

Figure 23:
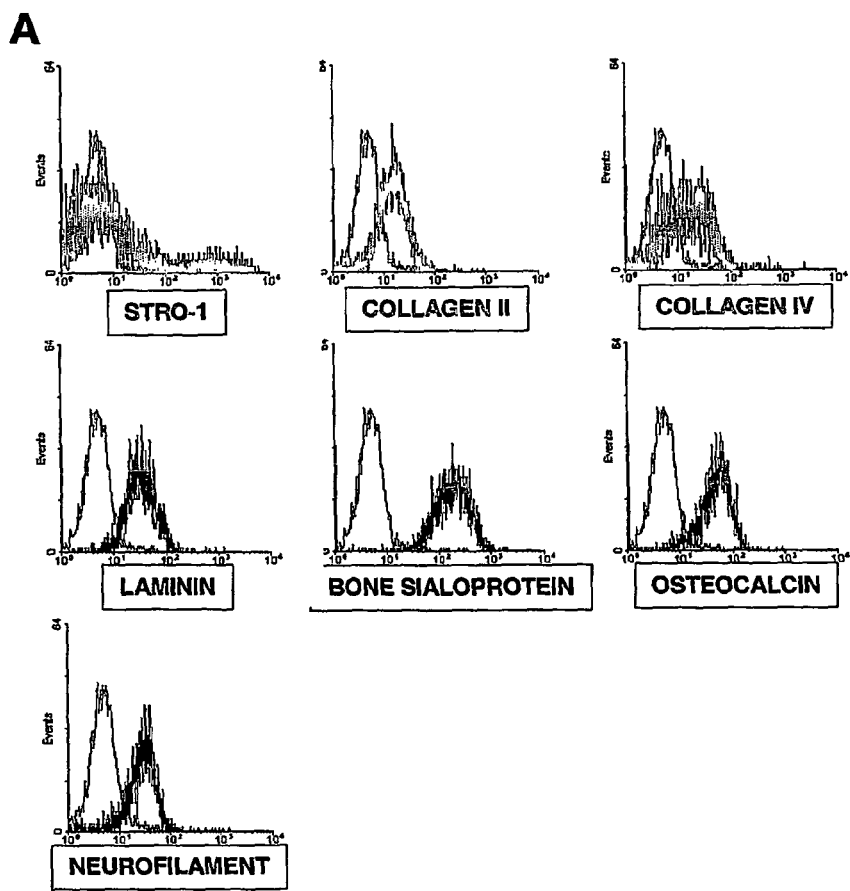
FIG. 23A. Immunophenotypic expression pattern of ex vivo expanded bone marrow MPC. Single cell suspensions of ex vivo expanded bone marrow MPC were prepared by trypsin/EDTA treatment then incubated with antibodies identifying cell lineage-associated markers. For those antibodies identifying intracellular antigens, cell preparations were fixed with cold 70% ethanol to permeabilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker (bold line) with reference to the isotype matched negative control antibodies (thin line).
FIG. 23B. Gene expression profile of cultured MPC. Single cell suspensions of ex vivo expanded bone marrow MPC were prepared by trypsin/EDTA treatment and total cellular RNA was prepared. Using RNAzolB extraction method total RNA was isolated and used as a template for cDNA synthesis, prepared using standard procedure. The expression of various transcripts was assessed by PCR amplification, using a standard protocol as described previously (Gronthos et al. 2003). Primers sets used in this study are shown in Table 2. Following amplification, each reaction mixture was analysed by 1.5% agarose gel electrophoresis, and visualised by ethidium bromide staining. Relative gene expression for each cell marker was assessed with reference to the expression of the house-keeping gene, GAPDH, using ImageQuant software.
Figure 23:
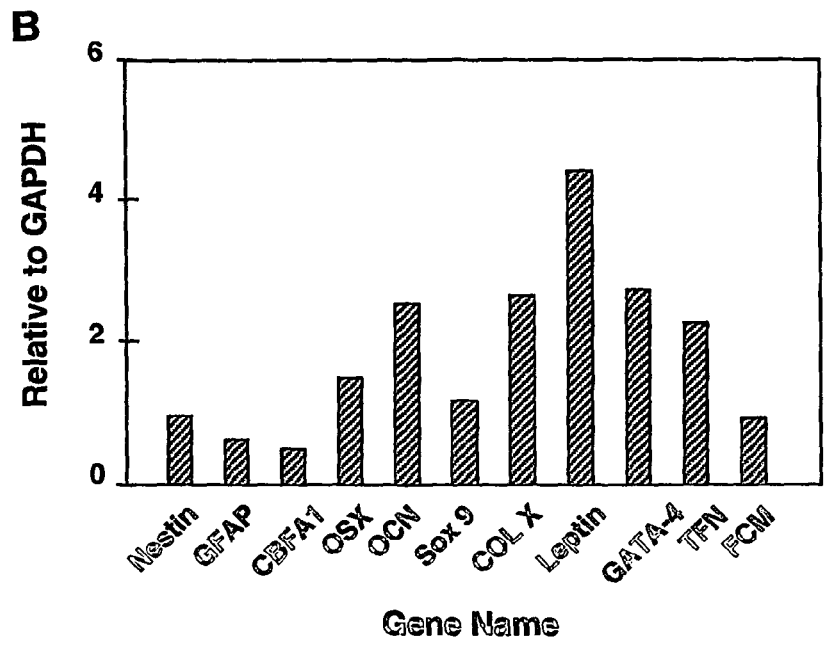

In the first series of experiments, semi-quantitative RT-PCR analysis was employed to examine the gene expression profile of various lineage-associated genes present in the cultured MPC populations (FIG. 23). Relative gene expression for each cell marker was assessed with reference to the expression of the house-keeping gene, GAPDH, using ImageQuant software (FIG. 23B). In addition, single-colour flow cytometric analysis was used to examine the protein expression profile of ex vivo expanded MPC based on their expression of cell lineage-associated markers (FIG. 23A). A summary of the general phenotype based on the gene and protein expression of the cultured MPC is presented in Table 1. Direct comparison of the gene expression profile of MPC described in the present patent demonstrated clear differences between this cell population and mesenchymal stem cells (MSC) previously described by Pittenger et al. 1999, (Table 1).

Unless otherwise indicated the materials and methods of this example are the same as those for Example 1.

FIG. 23A. Immunophenotypic expression pattern of ex vivo expanded bone marrow MPC. Single cell suspensions of ex vivo expanded bone marrow MPC were prepared by trypsin/EDTA treatment then incubated with antibodies identifying cell lineage-associated markers. For those antibodies identifying intracellular antigens, cell preparations were fixed with cold 70% ethanol to permeanbilize the cellular membrane prior to staining for intracellular markers. Isotype matched control antibodies were treated under identical conditions. Flow cytometric analysis was performed using a COULTER EPICS instrument. The dot plots represent 5,000 listmode events indicating the level of fluorescence intensity for each lineage cell marker (bold line) with reference to the isotype matched negative control antibodies (thin line).

FIG. 23B. Gene expression profile of cultured MPC. Single cell suspensions of ex vivo expanded bone marrow MPC were prepared by trypsin/EDTA treatment and total cellular RNA was prepared. Using RNAzolB extraction method total RNA was isolated and used as a template for cDNA synthesis, prepared using standard procedure. The expression of various transcripts was assessed by PCR amplification, using a standard protocol as described previously (Gronthos et al. 2003). Primers sets used in this study are shown in Table 2. Following amplification, each reaction mixture was analysed by 1.5% agarose gel electrophoresis, and visualised by ethidium bromide staining. Relative gene expression for each cell marker was assessed with reference to the expression of the house-keeping gene, GAPDH, using ImageQuant software.

Figure 22:
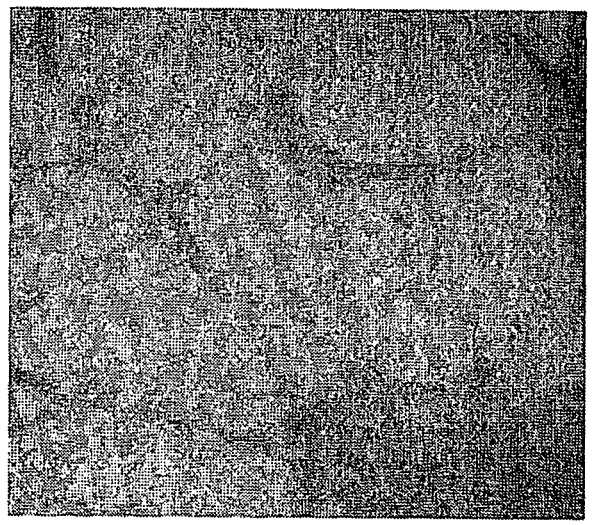
FIG. 22. Ex vivo expanded STRO-1$^{bright}$ MPC can develop into arterioles in vitro. Single cell suspensions of ex vivo expanded bone marrow STRO-1$^{bri}$ MPC were prepared by trypsin/EDTA treatment then plated into 48-well plates containing 200 µl of matrigel. The STRO-1$^{bri}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% CO$_2$, the wells were washed then fixed with 4% paraformaldehyde. Immunohistochemical studies were subsequently performed demonstrated that the cord-like structures expressed alpha-smooth muscle actin identified with a goat-anti-murine IgG horse radish peroxidase antibody.

FIG. 22. Ex vivo expanded STRO-1$^{bri}$ MPC can develop into arterioles in vitro. Single cell suspensions of ex vivo expanded bone marrow STRO-1$^{bri}$ MPC were prepared by trypsin/EDTA treatment then plated into 48-well plates containing 200 μl of matrigel. The STRO-1$^{bri}$ MPC were plated at 20,000 cells per well in serum-free medium (Gronthos et al. 2003) supplemented with the growth factors PDGF, EGF, VEGF at 10 ng/ml. Following 24 hours of culture at 37° C. in 5% $CO_2$, the wells were washed then fixed with 4% paraformaldehyde. Immunohistochemical studies were subsequently performed demonstrated that the cord-like structures expressed alpha-smooth muscle actin identified with a goat-anti-murine IgG horse radish peroxidase antibody.

TABLE 1

Comparison between cultured human Mesenchymal Precursor Cells (MCP's) and cultured human Mesenchymal Stem Cells (MSC's) following ex vivo expansion. Antigens found to be present on cell surface, intracellular or in the extra cellular matrix. MPCs express markers of tissues with different developmental origin, ie. ECT—ectoderm, MES—mesoderm and END—endoderm.

| ANTIGEN | MSC | MPC | Differentiated Cell Type. |
|---|---|---|---|
| STRO-1 | −ve | +ve | |
| Collagen II | −ve | +ve | Chondrocyte (MES) |
| Collagen IV | −ve | +ve | Fibroblast (MES) |
| Laminin | −ve | +ve | Fibroblast (MES) |
| Bone Sialoprotein (BSP) | −ve | +ve | Osteoblast (MES) |
| Osteocalcin (OCN) | −ve | +ve | Osteoblast (MES) |
| Nestin | ND | +ve | Neural (ECT) |
| Glial Fibrillary Acidic Protein (GFAP) | ND | +ve | Neural (ECT) |
| CBFA1 | −ve | +ve | Osteoblast (MES) |
| Osterix (OSX) | ND | +ve | Osteoblast (MES) |
| Osteocalcin (OCN) | −ve | +ve | Osteoblast (MES) |
| Sox9 | ND | +ve | Chondrocyte (MES) |
| Collagen X (COL X) | +ve | +ve | Chondrocyte (MES) |
| Leptin | ND | +ve | Adipose (MES) |

TABLE 1-continued

Comparison between cultured human Mesenchymal Precursor Cells (MCP's) and cultured human Mesenchymal Stem Cells (MSC's) following ex vivo expansion. Antigens found to be present on cell surface, intracellular or in the extra cellular matrix. MPCs express markers of tissues with different developmental origin, ie. ECT—ectoderm, MES—mesoderm and END—endoderm.

| ANTIGEN | MSC | MPC | Differentiated Cell Type. |
|---|---|---|---|
| GATA-4 | ND | +ve | Cardiomyocyte (MES) |
| Transferrin (TFN) | ND | +ve | Hepatocyte (END) |
| Flavin Containing Monooxygenase (FCM) | ND | +ve | Hepatocyte (END) |

TABLE 2

RT-PCR primers and conditions for the specific amplification of human mRNA

| Target Gene | Sense/Antisense (5'-3') Primer Sequences | Product Size |
|---|---|---|
| GAPDH | CACTGACACGTTGGCAGTGG/ [SEQ ID NO. 7] CATGGAGAAGGCTGGGGCTC [SEQ ID NO. 8] | 417 |
| Leptin | ATGCATTGGGAACCCTGTGC/ [SEQ ID NO.9] GCACCCAGGGCTGAGGTCCA [SEQ ID NO. 10] | 492 |
| CBFA-1 | GTGGACGAGGCAAGAGTTTCA/ [SEQ ID NO. 11] TGGCAGGTAGGTGTGGTAGTG [SEQ ID NO. 12] | 632 |
| OCN | ATGAGAGCCCTCACACTCCTC/ [SEQ ID NO. 13] CGTAGAAGCGCCGATAGGC [SEQ ID NO. 14] | 289 |
| GFAP | CTGTTGCCAGAGATGGAGGTT/ [SEQ ID NO. 15] TCATCGCTCAGGAGGTCCTT [SEQ ID NO. 16] | 370 |
| Nestin | GGCAGCGTTGGAACAGAGGTTGGA/ [SEQ ID NO. 17] CTCTAAACTGGAGTGGTCAGGGCT [SEQ ID NO. 18] | 460 |
| GATA-4 | GACTTCTCAGAAGGCAGAG/ [SEQ ID NO. 19] CTATCCTCCAAGTCCCAGAG [SEQ ID NO. 20] | 800 |
| PDGFβ-R | AATGTCTCCAGCACCTTCGT/ [SEQ ID NO. 21] AGCGGATGTGGTAAGGCATA [SEQ ID NO. 22] | 650 |
| Osterix | GGCACAAAGAAGCCGTACTC/ [SEQ ID NO. 23] CACTGGGCAGACAGTCAGAA [SEQ ID NO. 24] | 247 |
| COL X | AGCCAGGGTTGCCAGGACCA/ [SEQ ID NO. 25] TTTTCCCACTCCAGGAGGGC [SEQ ID NO. 26] | 387 |
| SOX9 | CTC TGC CTG TTT GGA CTT TGT/ [SEQ ID NO. 27] CCT TTG CTT GCC TTT TAC CTC [SEQ ID NO. 28] | 598 |

TABLE 2-continued

RT-PCR primers and conditions for the specific amplification of human mRNA

| Target Gene | Sense/Antisense (5'-3') Primer Sequences | Product Size |
|---|---|---|
| Ang-1 | CCAGTCAGAGGCAGTACATGCTA AGAATTGAGTTA/ [SEQ ID NO. 29] GTTTTCCATGGTTTTGTCCCGCAGTA [SEQ ID NO. 30] | 300 |

REFERENCES

1. Spradling et al., (2001). *Nature* 414(6859):98-104.
2. Bianco and Robey (2001) *Nature* 414(6859):118-121.
3. Fuchs and Segre (2000) *Cell* 100(1):143-55.
4. Gronthos et al., (2000) *Proc Natl Acad Sci USA* 97(25): 13625-30.
5. Kuznetsov et al., (1997). *J Bone Miner Res* 12(9):1335-47.
6. Bianco et al, (2001) *Stem Cells* 19(3):180-92.
7. Lichtman (1981) *Exp Hematol* 9(4):391-410.
8. Weiss (1976) *Anatomical Record* 186:161-84.
9. Weiss and Sakai H (1984) *Am J Anat* 170(3):447-63.
10. Dexter and Shadduck (1980) *J Cell Physiol* 102(3):279-86.
11. Orchardson amd Cadden (2001) *Dent Update* 28(4):200-6, 208-9.
12. Peters and Balling (1999) *Trends Genet* 15(2):59-65.
13. Thesleff and Aberg (1999) *Bone* 25(1):123-5.
14. Friedenstein et al., (1974) *Transplantation* 17(4):331-40.
15. Castro-Malaspina et al., (1980) *Blood* 56(2):289-301.
16. Weissman (2000) *Cell* 100(1):157-68.
17. Uchida et al., (2000) *Proc Natl Acad Sci USA* 97(26): 14720-5.
18. Kuznetsov et al., (2001) *J Cell Biol* 153(5):1133-40.
19. Shi et al. (2001) *Bone* 29(6):532-39.
20. Pittenger et al., (1999) *Science* 284(5411):143-7.
21. Gronthos et al., (2002) *J Dent Res* 81(8):531-5.
22. Owen and Friedenstein (1988) *Ciba Found Symp* 136(29): 42-60.
23. Doherty et al., (1998) *J Bone Miner Res* 13(5):828-38.
24. Bianco and Cossu (1999). *Exp Cell Res* 251(2):257-63.
25. Gronthos et al., (1998) Isolation, purification and in vitro manipulation of human bone marrow stromal precursor cells. In: Beresford J N and Owen M E (ed) Marrow stromal cell culture. Cambridge University Press, Cambridge, UK, pp 26-42.
26. Gronthos and Simmons (1995) *Blood* 85(4):929-40.
27. Gronthos et al., (1999) *J Bone Miner Res* 14(1):47-56.
28. Filshie et al., (1998) *Leukemia* 12(3):414-21.
29. Simmons and Torok-Storb (1991). *Blood* 78(1):55-62.
30. Canfield and Schor (1998) Osteogenic potential of vascular pericytes. In: Beresford J N and Owen M E (ed) Marrow stromal cell culture. Cambridge University Press, Cambridge, UK, pp 128-148.
31. Riminucci and Bianco (1998) The bone marrow stroma in vivo: ontogeny, structure, cellular composition and changes in disease. In: Beresford J N and Owen M E (ed) Marrow stromal cell culture. Cambridge University Press, UK, Cambridge, UK, pp 10-25.
32. Gronthos et al., (1994) *Blood* 84(12):4164-73.
33. Oyajobi et al, (1999) *J Bone Miner Res* 14(3):351-61.
34. Dennis et al., (2002). *Cells Tissues Organs* 170(2-3):73-82.
35. Stewart et al., (1999) *J Bone Miner Res* 14(8):1345-56.
36. Ahdjoudj et al., (2001)*J Cell Biochem* 1(1):23-38.
37. Shih (1999) *J Pathol* 189(1):4-11.
38. Van Vlasselaer et al., (1994) *Blood* 84(3):753-63.
39. Prockop et al., (2001). *Cytotherapy* 3(5):393-6.
40. Ducy et al., (1997) *Cell* 89(5):747-54.
41. Komori et al., (1997) *Cell* 89(5):755-64.
42. Woodbury et al., (2000) *J Neurosci Res* 61(4):364-70.
43. Dey et al., (2001) *Arch Oral Biol* 46(3):249-60.
44. Ueno et al., (2001) *Matrix Biol* 20(5-6):347-55.
45. Couble et al., (2000) *Calcif Tissue Int* 66(2):129-38.
46. Nehls and Drenckhahn (1993) *Histochemistry* 99(1):1-12.
47. Schor et al., (1995) *Clin Orthop* 313:81-91.
48. Pugach et al., (1999) *Arkh Patol* 61(4):18-21.
49. Nehls et al., (1992) *Cell Tissue Res* 270(3):469-74.
50. Brighton et al., (1992) *Clin Orthop* 275:287-99.
51. Nayak et al., (1988) *J Exp Med* 167(3):1003-15.
52. Andreeva et al., (1998) *Tissue Cell* 30(1):127-35.
53. Cattoretti et al., (1993) *Blood* 81(7):1726-38.
54. Charbord et al., (2000) *J Hemather Stem Cell Res* 9(6): 935-43.
55. Dennis and Charbord (2002) *Stem Cells* 20(3):205-14.
56. Young et al., (2001) *Anat Rec* 263(4):350-60.

Gronthos et al., (2003). *Journal of Cell Science* 116: 1827-1835.
Pittenger et al., (1999). *Science* 284, 143-7.
Simmons and Torok-Storb (1991a). *Blood* 78(1):55-62.
Simmons and Torok-Storb (1991b). *Blood* 78:2848.
Shi and Gronthos. (2003). *Journal of Bone and Mineral Research,* 18(4): 696-704.

The invention claimed is:

1. A method of inducing formation or repair of blood vessels in an ischemic first tissue, comprising contacting the ischemic first tissue with a population of cells which has been enriched for mesenchymal precursor cells (MPCs) that express the markers STRO-1, CD146, and alpha smooth muscle actin but are negative for CD34, CD45, and glycophorin A, so as to thereby induce formation of blood vessels or repair of existing blood vessels in the ischemic first tissue.

2. The method of claim 1 wherein the population of cells comprises at least 0.01% MPCs capable of forming a clonogenic colony.

3. The method of claim 1 wherein the population of cells comprises at least 0.1% MPCs capable of forming a clonogenic colony.

4. The method of claim 1 wherein the population of cells comprises at least 0.01% STRO-1$^{bright}$ MPCs.

5. The method of claim 1 wherein the population of cells comprises at least 0.1% STRO-1$^{bright}$ MPCs.

6. The method of claim 1 wherein the population of cells comprises at least 1% STRO-1$^{bright}$ MPCs.

7. The method of claim 1 wherein the MPCs that express the marker STRO-1 additionally co-express the marker VCAM-1.

8. The method of claim 1 wherein the population of cells is derived from a second tissue selected from the group consisting of skin, liver, kidney, heart, adipose tissue, teeth, dental pulp, retina, brain, hair follicles, intestine, lung, spleen, lymph node, thymus, pancreas, bone, ligament, bone marrow, tendon, and skeletal muscle.

9. The method of claim 1 wherein the population of cells is isolated from a perivascular niche within a vascularised tissue source.

10. The method of claim 1 wherein the population of cells is isolated from a perivascular niche within a non-haemopoietic vascularised tissue.

11. The method of claim 1 wherein the population of cells comprises at least 10% STRO-1$^{bright}$ MPCs.

12. The method claim 1 wherein the MPCs that express the marker STRO-1 co-express any one or more of the markers selected from the group consisting of THY-1, VCAM-1, ICAM-1, PECAM-1, CD49a/CD49b/CD29, CD49c/CD29, CD49d/CD29, CD29, CD61, integrin beta5, 6-19, thrombomodulin, CD10, CD13, SCF, PDGF-R, EGF-R, IGF-1R, NGF-R, FGF-R and Leptin-R (STRO-2).

13. A method of inducing neovascularisation in a target ischemic tissue of a patient, the method comprising the step of administering to the target ischemic tissue an effective amount of a population of human mesenchymal precursor cells (MPCs) which has been enriched for cells that express the markers STRO-1, CD146, and alpha smooth muscle actin but are negative for CD34, CD45, and glycophorin A.

14. The method according to claim 12, wherein the target tissue is cardiac tissue.

15. The method of claim 1, wherein the ischemic tissue is in a subject suffering from cerebrovascular ischemia, renal ischemia, pulmonary ischemia, limb ischemia, ischemic cardiomyopathy, or myocardial ischemia.

16. The method of claim 1, wherein the MPCs that express the marker STRO-1 are human.

17. The method of claim 1, further comprising seeding the purified populations of human cells in a matrix prior to contacting the first tissue.

18. The method of claim 17, wherein the matrix is a scaffold.

19. The method of claim 18, wherein the scaffold induces differentiation of the population of human cells.

20. The method of claim 1, further comprising contacting the ischemic first tissue with a compound known to promote formation or repair of blood vessels.

21. The method of claim 13, wherein the population of cells comprises at least 0.01% MPCs capable of forming a clonogenic colony.

22. The method of claim 13, wherein the population of cells comprises at least 0.1% MPCs capable of forming a clonogenic colony.

23. The method of claim 21, wherein the population of cells comprises at least 0.01% STRO-1$^{bright}$ MPCs.

24. The method of claim 22, wherein the population of cells comprises at least 0.1% STRO-1$^{bright}$ MPCs.

25. The method of claim 13, wherein the population of cells comprises at least 1% STRO-1$^{bright}$ MPCs.

26. The method of claim 25, wherein the MPCs that express the marker STRO-1 additionally co-express the marker VCAM-1.

27. The method of claim 25, wherein the population of cells is derived from a second tissue of the patient selected from the group consisting of skin, liver, kidney, heart, adipose tissue, teeth, dental pulp, retina, brain, hair follicles, intestine, lung, spleen, lymph node, thymus, pancreas, bone, ligament, tendon, and skeletal muscle.

28. The method of claim 25, wherein the population of cells is isolated from a perivascular niche within a vascularised tissue source.

29. The method of claim 25, wherein the population of cells is isolated from a perivascular niche within a non-haemopoietic vascularised tissue.

30. The method of claim 25, further comprising seeding the population of human cells in a matrix prior to contacting the first tissue.

31. The method of claim 30, wherein the matrix is a scaffold.

32. The method of claim 31, wherein the scaffold induces differentiation of the population of human cells.

33. The method of claim 25, further comprising administering to the patient a compound known to promote formation or repair of blood vessels.

34. The method of claim 33, wherein the population of human MPCs and the compound known to promote formation or repair of blood vessels are coadministered.

35. The method of claim 1, wherein the enriched population is cultured and/or expanded prior to contacting the ischemic first tissue.

36. The method of claim 13, wherein the enriched population is cultured and/or expanded prior to contacting the ischemic first tissue.

* * * * *